US009872917B2

(12) United States Patent
Tang et al.

(10) Patent No.: US 9,872,917 B2
(45) Date of Patent: Jan. 23, 2018

(54) ANION-PAIRED CATIONIC METALLOCENE-CONTAINING COMPOUNDS AND POLYMERS AS ANTIMICROBIAL AGENTS

(71) Applicant: University of South Carolina, Columbia, SC (US)

(72) Inventors: Chuanbing Tang, Columbia, SC (US); Jiuyang Zhang, West Columbia, SC (US); Yung-Pin Chen, Columbia, SC (US); Alan W. Decho, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 15/194,724

(22) Filed: Jun. 28, 2016

(65) Prior Publication Data
US 2017/0080096 A1 Mar. 23, 2017

Related U.S. Application Data

(62) Division of application No. 14/245,445, filed on Apr. 4, 2014, now Pat. No. 9,402,394.

(60) Provisional application No. 61/961,527, filed on Oct. 17, 2013, provisional application No. 61/808,436, filed on Apr. 4, 2013.

(51) Int. Cl.
| | |
|---|---|
| *A01N 55/02* | (2006.01) |
| *A61K 31/43* | (2006.01) |
| *A61K 31/546* | (2006.01) |
| *C08F 220/28* | (2006.01) |
| *C08F 275/00* | (2006.01) |
| *A61K 47/48* | (2006.01) |
| *A01N 37/12* | (2006.01) |

(52) U.S. Cl.
CPC ........ *A61K 47/48176* (2013.01); *A01N 37/12* (2013.01); *A01N 55/02* (2013.01); *A61K 31/43* (2013.01); *A61K 31/546* (2013.01); *C08F 220/28* (2013.01); *C08F 2220/282* (2013.01)

(58) Field of Classification Search
CPC ......... A01N 37/12; C07F 17/00; C07F 17/02; C08F 230/04; C08F 130/04
See application file for complete search history.

(56) References Cited

U.S. PATENT DOCUMENTS

| | | |
|---|---|---|
| 8,592,539 B2 | 11/2013 | Tang |
| 2011/0086979 A1 | 4/2011 | Tang |
| 2012/0041163 A1 | 2/2012 | Tang et al. |
| 2012/0214950 A1 | 8/2012 | Tang et al. |

FOREIGN PATENT DOCUMENTS

WO    WO 2006052427    5/2006

OTHER PUBLICATIONS

Horcajada et al., "Metal-Organic Frameworks in Biomedicine", Chem. Rev. 112, 2012, 1232-1268.
Murray et al., "Organometallic Anticancer Agents: The Effect of the Central Metal and Halide Ligands on the Interaction of Metallocene Dihalides $Cp_2MX_2$ with Nucleic Acid Constituents", J. Med. Chem. 37, 1994, 1936-1941.
Della Rocca et al., "Nanoscale Metal-Organic Frameworks for Biomedical Imaging and Drug Delivery", Accounts of Chemical Research, vol. 44, No. 10, 2011, 957-968.
Ren et al., "Synthesis and Solution Self-Assembly of Side-Chain Cobaltocenium-Containing Block Copolymers", J. Am. Chem. Soc. 132, 2010, 8874-8875.
Noor et al., "A Cobaltocenium-Peptide Bioconjugate Shows Enhanced Cellular Uptake and Directed Nuclear Delivery", Angew. Chem. Int. Ed. 44, 2005, 2429-2432.
Qiu et al., "DNA-induced chirality in water-soluble poly(cobaltoceniumethylene)", Chem. Commun. 49, 2013, 42-44.
Hapiot et al., "Cyclodextrins as Supramolecular Hosts for Organometallic Complexes", Chemical Reviews, vol. 106, No. 3, Feb. 21, 2006, 767-781.
Boman, Hans G., "Antibacterial Peptides: Key Components Needed in Immunity", Cell, vol. 65, Apr. 19, 1991, 205-207.
Brogden, Kim A., "Antimicrobial Peptides: Pore Formers or Metabolic Inhibitors in Bacteria?", Nature Reviews Microbiology, vol. 3, Mar. 2005, 238-250.
Nederberg et al., "Biodegradable nanostructures with selective lysis of microbial membranes", Nature Chemistry, vol. 3, May 2011, 409-414.
Li et al., "A polycationic antimicrobial and biocompatible hydrogel with microbe membrane suctioning ability", Nature Materials, vol. 10, Feb. 2011, 149-156.
Gabriel et al., "Infectious disease: Connecting innate immunity to biocidal polymers", Materials Science and Engineering R-Reports 57, 2007, 28-64.
Kenawy et al., "The Chemistry and Applications of Antimicrobial Polymers: A State-of-the-Art Review", Biomacromolecules, vol. 8, No. 5, 2007, 1359-1384.
Tashiro, Tatsuo, "Antibacterial and Bacterium Adsorbing Macromolecules", Macromolecular Materials and Engineering 286, 2001, 63-87.
Gasser et al., "Organometallic Anticancer Compounds", J. Med. Chem. 54, 2011, 3-25.
Patra et al., "Sandwich and Half-Sandwich Derivatives of Platensimycin: Synthesis and Biological Evaluation", Organometallics 31, 2012, 5760-5771.
Harding et al., Organometallic Anticancer Agents. 2. Aqueous Chemistry and Interaction of Niobocene Dichloride with Nucleic Acid Constituents and Amino Acids, J. Med. Chem. 39, 1996, 5012-5016.

(Continued)

*Primary Examiner* — Irina S Zemel
*Assistant Examiner* — Jeffrey Lenihan
(74) *Attorney, Agent, or Firm* — Dority & Manning, PA

(57) ABSTRACT

Anion-paired metallocene-containing compounds are generally provided, along with methods of making the same. In one embodiment, the anion-paired metallocene-containing compound includes a cationic metallocene moiety covalently connected to an organic functional group, and an anion paired to the cationic metallocene moiety. Generally, the cationic metallocene moiety comprises two cyclopentadienyl anions bound to a metal center in the oxidation state I.

6 Claims, 24 Drawing Sheets

(56) References Cited

OTHER PUBLICATIONS

Zhang et al., "Cobaltocenium-Containing Methacrylate Homopolymers, Block Copolymers, and Heterobimetallic Polymers via RAFT Polymerization", Macromolecules 45, 2012, 6857-6863.

Sheehan et al., "The Total Synthesis of Penicillin V", Journal of the American Chemical Society 79, 1957, 1262-1263.

French, G.L., "The continuing crisis in antibiotic resistance", International Journal of Antimicrobial Agents 36, S3, 2010, S3-S7.

Coates et al., "The Future Challenges Facing the Development of New Antimicrobial Drugs", Nature Reviews Drug Discovery, vol. 1, Nov. 2002, 895-910.

Guignard et al., "β-lactams against methicillin-resistant *Staphylococcus aureus*" Current Opinion in Pharmacology 5, 2005, 479-489.

Rogers et al., "Synergistic Effects between Conventional Antibiotics and 2-Aminoimidazole-Derived Antibiofilm Agents", Antimicrobial Agents and Chemotherapy, vol. 54, No. 5, 2112-2118.

Norris et al., "Production of A and C Variants of Staphylococcal β-Lactamase by Methicillin-Resistant Strains of *Staphylococcus aureus*" Antimicrobial Agents and Chemotherapy, vol. 38, No. 7, Jul. 1994, p. 1649-1650.

Liu et al., "Main-chain imidazolium oligomer material as a selective biomimetic antimicrobial agent", Biomaterials 33, 2012, 8625-8631.

Ren, Lixia et al. Chemical Science vol. 3 pp. 580-583 Published online Nov. 2011.

Ren, Lixia et al. Macromolecular Rapid Communications col. 33 pp. 510-516 Published Jan. 2012.

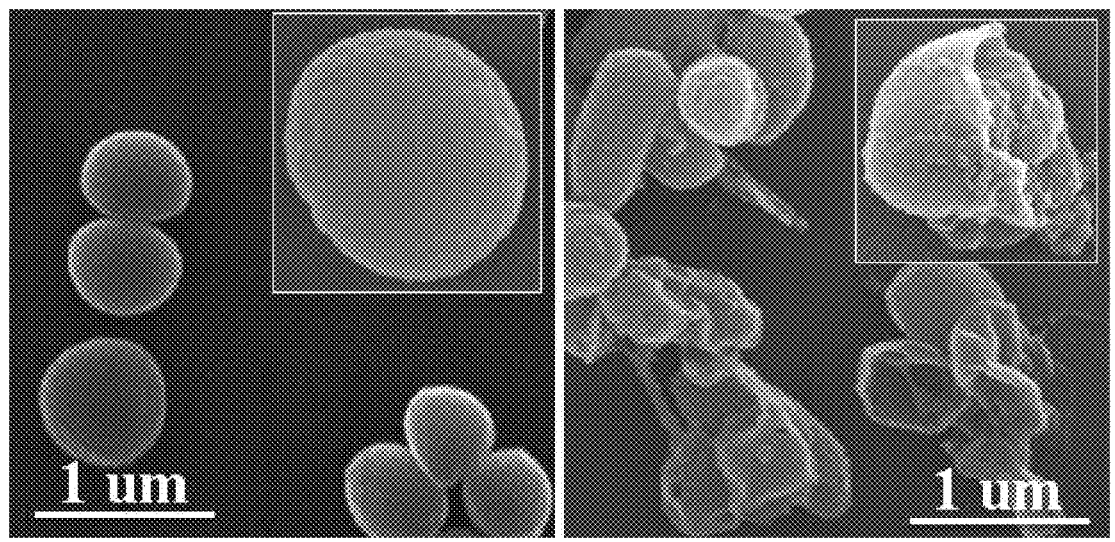
*Fig. 5A*      *Fig. 5B*
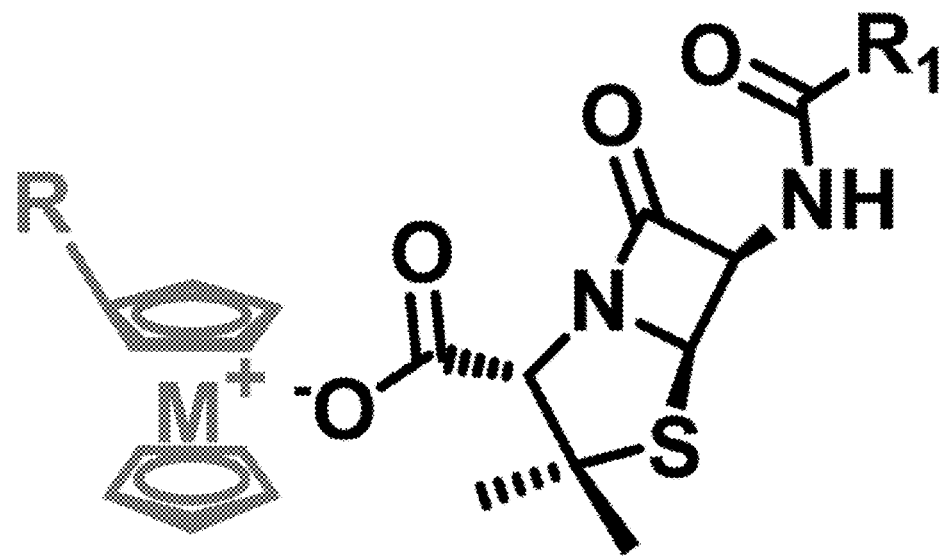
*Fig. 6A*

| | Cl⁻ | Br⁻ | I⁻ | PF₆⁻ |
|---|---|---|---|---|
| HA-MRSA | 5.00 | 5.00 | 10.0 | x |
| CA-MRSA | 5.00 | 3.00 | x | x |
| MRSA-252 | 5.00 | 5.00 | 5.00 | 10.0 |
| MSSA | 1.00 | 1.00 | x | x |

*Fig. 15A*

ANION-PAIRED CATIONIC METALLOCENE-CONTAINING COMPOUNDS AND POLYMERS AS ANTIMICROBIAL AGENTS

PRIORITY INFORMATION

The present application claims priority to and is a divisional application of U.S. patent application Ser. No. 14/245,445 titled "Anion-Paired Cationic Metallocene-Containing Compounds and Polymers as Antimicrobial Agents" of Tang, et al. filed on Apr. 4, 2014, which claims priority to U.S. Provisional Patent Application Ser. No. 61/808,436 titled "Anion-Paired Cationic Metallocene-Containing Compounds and Polymers as Antimicrobial Agents" of Tang, et al. filed on Apr. 4, 2013, and to U.S. Provisional Patent Application Ser. No. 61/961,527 titled "Metallocene-Containing Cationic Compounds and Polymers Loaded with Antibiotics as Antimicrobial" of Tang, et al. filed on Oct. 17, 2013, the disclosures of which are incorporated by reference herein.

GOVERNMENT SUPPORT CLAUSE

This invention was made with government support under CHE 1151479 awarded by National Science Foundation. The government has certain rights in the invention.

BACKGROUND

In the last past two decades, organometallic compounds and polymers have been introduced into various applications of medicinal chemistry such as the use as drugs, drug delivery substrates and enzyme inhibitors, due to unique properties from metal centers and specially-designed organic frameworks. Among various organometallic molecules, cationic metallocene moieties have been considered as promising candidates for new biomaterials due to their high stability, unique redox property and potential bioactivity. Cationic metallocene-containing molecules now have been utilized into a broad field of clinical studies, such as the using as anticancer drugs, novel targeting agents and new DNA cooperation compounds. On the other hand, considering the ability to disrupt the bacterial pathogen cytoplasmic membrane and low drug resistance from cationic polymers, introduction of cationic molecules into polymer frameworks have attracted lots of attention in recent years. Cationic polymers now have many applications such as antimicrobial materials, antifouling coatings, packaging materials, and drug delivery materials. However, as a type of cationic polymers, cationic metallopolymers are far less explored as biomaterials, which have been limited by the challenging synthetic methods and the difficulty controlling the stability and toxicity of these metal elements. As a result, considering the advantages from cationic metallocene moieties and cationic polymer frameworks, the combination of cationic metallocene moieties and polymers would offer distinguished biomaterials, which have a great potential to construct novel and effective drugs and antimicrobial materials.

Traditional antibiotics, such as penicillins, have been utilized for human health care for decades. However, bacteria are now more and more resistant towards these drugs. Some superbugs, such as Methicillin-resistant *Staphylococcus aureus* (MRSA) (community-associated (CA-MRSA), hospital-associated (HA-MRSA) and MRSA-252), show extremely high resistance towards most of current antibiotics. To overcome such challenge, many efforts have been made, such as modification of conventional antibiotics and design of new antimicrobial drugs. Among them, one of the most convenient methods is to find new inhibitors to activate traditional antibiotics.

For example, in an effort to circumvent antibiotic resistance, β-lactamase inhibitors, including boronic acid derivatives, phosphonates and phosphonamidates, have been designed, although none of these agents have entered Phase I development. Alternatively, synthetic macromolecules have been introduced as antimicrobial agents. Rather than targeting penicillin-binding proteins (PBP) as the most β-lactam antibiotics do, cationic polymers or peptides can disrupt thick cell walls or membranes, and have shown efficacy against MRSA. Some conventional antibiotics have exhibited activity against MRSA by their modification with polymers via covalent bonds or encapsulation in a polymeric matrix. However, most of these strategies have been restricted by their inherent limitations, such as the high toxicity of cationic polymers and peptides, poor release of antibiotics, and relatively low targeting efficiency toward bacteria. In contrast, organometallic compounds and macromolecules have been previously used as anticancer drugs, targeting agents, and enzyme inhibitors. However, their use as antimicrobial materials still remains in the early stages, and most have not yet achieved an optimal balance between toxicity and bioactivity.

For example, cationic polymers have been utilized into many applications, such as antimicrobial materials, antifouling coatings, packaging materials, drug delivery materials. Among them, cationic metallocene-containing polymers are promising candidates for novel medicinal materials due to their unique properties from their metal centers and special frameworks. Though a lot of medical applications from cationic metallocene-containing compounds and polymers, only a few of them reported the utilization as antimicrobial materials. None of the work involves the loading of conventional antibiotics by cationic metallocene-containing materials to inhibit bacterial pathogens.

SUMMARY

Objects and advantages of the invention will be set forth in part in the following description, or may be obvious from the description, or may be learned through practice of the invention.

Anion-paired metallocene-containing compounds are generally provided, along with methods of making the same. In one embodiment, the anion-paired metallocene-containing compound includes a cationic metallocene moiety covalently connected to an organic functional group, and an anion paired to the cationic metallocene moiety. Generally, the cationic metallocene moiety comprises two cyclopentadienyl anions bound to a metal center in the oxidation state I.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

FIG. 5A and FIG. 5B show, respectively, FE-SEM images of HA-MRSA cells before (FIG. 5A) and after (FIG. 5B) incubation with iodide-paired cobaltocenium-containing homopolymers (at 10 μM). The inserted pictures are the enlarged part of the cells for view purposes.

FIG. 6A shows an antibiotic-loaded metallocene-containing compound or polymer, with the anti-biotic shown as a penicillin or related compound, where M is a metal, R is a linker on metallocene (e.g., small molecule linkers, oligomer linkers and polymer linkers), and $R_1$ represents a functional group of the antibiotic (e.g., an organic functional group).

FIG. 15A shows a table of $IC_{90}$ values (μM) of $Cl^-$, $Br^-$, $I^-$ and $PF_6^-$-paired cobaltocenium-containing polymers against MSSA, HA-MRSA, CA-MRSA, and MRSA-252 from standard solution micro-broth measurement ("x" indicates less than 90% inhibition at 10 μM. For halide and $PF_6^-$-paired cobaltocenium-containing polymers, 1 μM is equal to 12.5~15.6 μg/mL, respectively.

DEFINITIONS

Figure 1A:
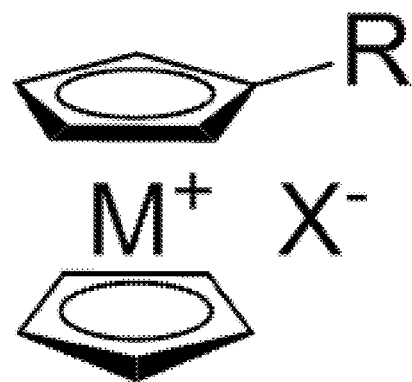
FIG. 1A illustrates an exemplary anion-paired metallocene-containing compound, where M is a metal, X is an anion, and R is a substituted group (e.g., an organic group).

Chemical elements are discussed in the present disclosure using their common chemical abbreviation, such as commonly found on a periodic table of elements. For example, hydrogen is represented by its common chemical abbreviation H; helium is represented by its common chemical abbreviation He; and so forth.

As used herein, the term "polymer" generally includes, but is not limited to, homopolymers; copolymers, such as, for example, block, graft, random and alternating copolymers; and terpolymers; and blends and modifications thereof. Furthermore, unless otherwise specifically limited, the term "polymer" shall include all possible geometrical configurations of the material. These configurations include, but are not limited to isotactic, syndiotactic, and random symmetries.

The term "organic" is used herein to refer to a class of chemical compounds that are comprised of carbon atoms. For example, an "organic polymer" is a polymer that includes carbon atoms in the polymer backbone, but may also include other atoms either in the polymer backbone and/or in side chains extending from the polymer backbone (e.g., oxygen, nitrogen, sulfur, etc.).

As used herein, the term "related compounds thereof" refers to compounds that have the base chemical structure but for substituted atom(s) and/or substituted side groups.

The term "pharmaceutically effective amount" refers to that amount of a drug or pharmaceutical agent that will elicit the biological or medical response of a tissue, system, animal, or human that is being sought by a researcher or clinician. This amount can be a therapeutically effective amount.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

An entirely new type of cationic organometallic compounds and metallopolymers are generally provided for biomedical applications, such as drugs and antimicrobial agents. Successful implementation of these organometallic compounds and their charged metallopolymers can offer effective antimicrobial agents against a broad spectrum of bacterial pathogens, including those showed resistance to conventional antibiotics. In one embodiment, the utilization of cationic metallocene (also called metallocenium) derivatives and their polymers as antimicrobial agents is generally provided. Such cationic metallocene-containing compounds and polymers have effective antimicrobial activities against a broad spectrum of bacterial pathogens, including Gram-positive and Gram-negative bacteria and many kinds of multidrug-resistant *Staphylococcus aureus* and methicillin-sensitive *Staphylococcus aureus*.

A metallocene is a compound having two cyclopentadienyl anions (Cp, which is $C_5H_5^-$) bound to a metal center (M) in the oxidation state II, with the resulting general formula $(C_5H_5)_2M$. Closely related to the metallocenes are the metallocene derivatives, (e.g. titanocene dichloride, vanadocene dichloride). However, a metallocene-containing cationic compound generally has a positive charge due to the metal center (M) being in the oxidation state I. Thus, the overall charge of the metallocene-containing cationic compound is +1, such that the metallocene-containing cationic compound is paired to an anion having a negative charge, such as hexafluorophosphate ($PF_6^-$), tetraphenylborate ($BPh_4^-$), tetrafluoroborate ($BF_4^-$), trifluoromethanesulfonate ($OTf^-$), $F^-$, $Cl^-$, $Br^-$, $I^-$, $NO_3^-$, acetate ($Ac^-$), sulfate ($SO_4^{2-}$), hydrogen sulfate ($HSO_4^-$), perchlorate ($ClO_4^-$), bromate ($BrO_3^-$), cyanide ($CN^-$), thiocyanate ($SCN^-$), hydroxide ($OH^-$), dihydrogen phosphate ($H_2PO_4^-$), or formate ($HCOO^-$).

Referring to FIG. 1A, a generic anion-paired metallocene-containing compound is shown, where M is a metal, X is an anion, and R is a substituted group (e.g., an organic group).

I. Anion-Paired Metallocene-Containing Monomers

Figure 1B:
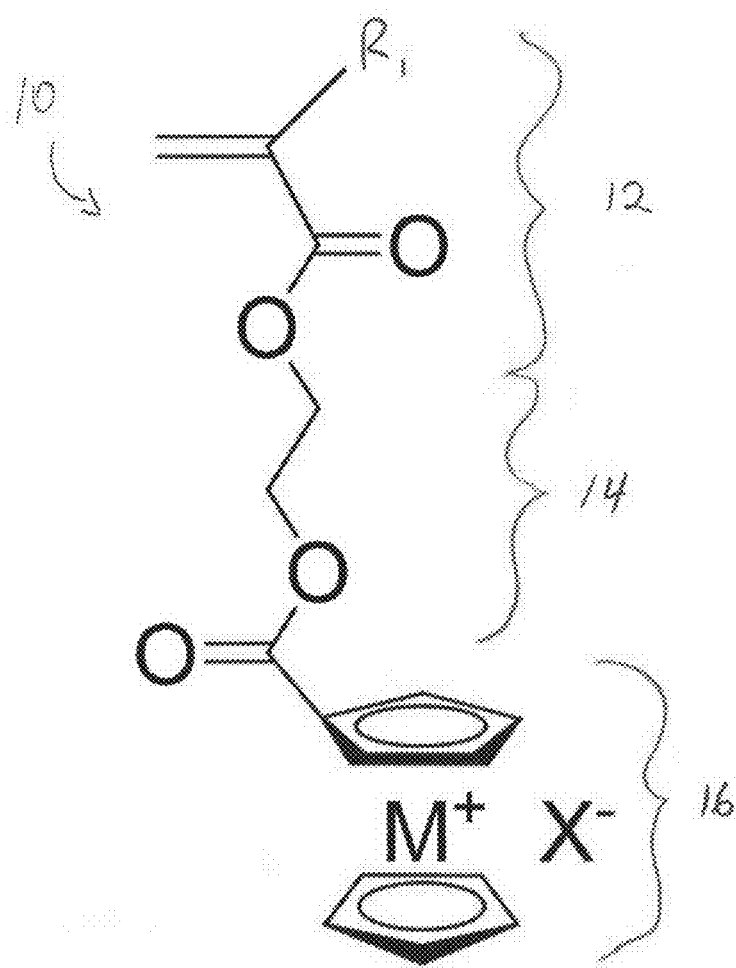
FIG. 1B illustrates an exemplary anion-paired metallocene-containing monomer, where M is a metal and X is an anion.

Generally, each anion-paired metallocene-containing monomer includes an anion-paired metallocene group covalently attached to a polymerizable group via an organic linker group. Referring to FIG. 1B, for example, an anion-paired metallocene-containing monomer 10 is shown, where M is a metal and X is an anion. The anion-paired metallocene-containing monomer 10 includes a polymerizable group 12 covalently attached to an anion-paired metallocene group 16 via an organic linker group 14.

a. Anion-Paired Metallocene Group

As stated above, a cationic metallocene group includes two cyclopentadienyl rings bound to a metal center (M) in an oxidation state, which is leave the cationic metallocene group with a positive charge (such as +1 or +2). Thus, the cationic metallocene group is generally paired with a counter ion. For example, an anion (X) can be present such that the charge of the resulting anion-paired cationic metallocene group is zero.

Particularly suitable metals, for use as the metal center (M), include iron (Fe), cobalt (Co), rhodium (Rh), ruthenium (Ru), etc. in their cationic state (i.e., a cationic metal center).

The anion ("X") paired with the cationic metallocene-containing compound can be any suitable anion, including, but not limited to, hexafluorophosphate ($PF_6^-$), tetraphenylborate ($BPh_4^-$), tetrafluoroborate ($BF_4^-$), trifluoromethanesulfonate ($OTf^-$), $F^-$, $Cl^-$, $Br^-$, $I^-$, $NO_3^-$, acetate ($Ac^-$), sulfate ($SO_4^{2-}$), hydrogen sulfate ($HSO_4^-$), perchlorate ($ClO_4^-$), bromate ($BrO_3^-$), cyanide ($CN^-$), thiocyanate ($SCN^-$), hydroxide ($OH^-$), dihydrogen phosphate ($H_2PO_4^-$), or formate ($HCOO^-$).

b. Organic Linker Group

Diverse organic linker groups 14 can be positioned between the polymerizable group 12 (i.e., containing the vinyl group) and the anion-paired metallocene group 16. In one embodiment, the organic linker group 14 includes a simple alkyl chain having a number (m) of repeating carbon atoms (each with two hydrogen atoms thereon, i.e., —$CH_2$—), with m being an integer of 1 to about 50, such as 2 to about 40 (e.g., about 2 to about 20). In one particular embodiment, m is about 2 to about 12. As shown in the embodiment of FIG. 1B, the organic linker group 14 includes an ethyl chain (i.e., an alkyl chain of 2 carbons).

The organic linker group 14 can also include any covalent linkage to one of the cyclopentadienyl rings of the anion-paired metallocene group 16, such as an ester linkage as shown in FIG. 1B.

Although not shown in the exemplary embodiment of FIG. 1B, the alkyl chain of the organic linker group 14 can be substituted with common substituents found on alkyl chains (e.g., hydroxyl groups, amine groups, etc.).

c. Polymerizable Groups

The polymerizable group 12 of the anion-paired metallocene-containing monomer 10 can include a vinyl group, such as an acrylic group, a methacrylic group, a styrenic group, an acrylamide group, or a norbornene group. For example, FIG. 1B shows an exemplary monomer 10 having a (meth)acrylic group forming its polymerizable group 12, with $R_1$ being either H (i.e., an acrylic group) or —$CH_3$ (i.e., a methacrylic group).

No matter the particular chemistry of the polymerizable group 12, a vinyl group is present and configured for polymerization into a polymeric chain.

d. Exemplary Monomer

FIG. 1B shows an exemplary anion-paired metallocene-containing monomer 10 that is, when $R_1$ is a methyl group, 2-(methacrylolyoxy)ethyl metalloceniumcarboxylate.

II. Anion-Paired Metallocene-Containing Polymers

Generally, each of the monomers discussed above can be polymerized to form a cationic polymer (including homopolymers, block copolymers, random copolymers, graft copolymers, star copolymers or organic/inorganic hybrids) that contains at least one unit derived from a cationic metallocene moiety. In one embodiment, anion-paired metallocene-containing polymers can be prepared by free radical and controlled/living radical polymerization of the vinyl-containing monomers. These polymers have an anion-paired metallocene moiety at the side-chain.

In one embodiment, the synthesis of side-chain anion-paired metallocene-containing polymers can be performed via free radical polymerization and/or controlled/living polymerization methods (e.g., RAFT, ROMP, etc., such as those described in U.S. Publication No. 2012/0214950 of Tang, et al. filed on Feb. 15, 2012; U.S. Publication No. 2012/0041163 of Tang, et al. filed on Aug. 15, 2011; and U.S. Publication No. 2011/0086979 of Tang filed on Oct. 8, 2010, the disclosures of which are incorporated by reference herein).

Figure 2A:
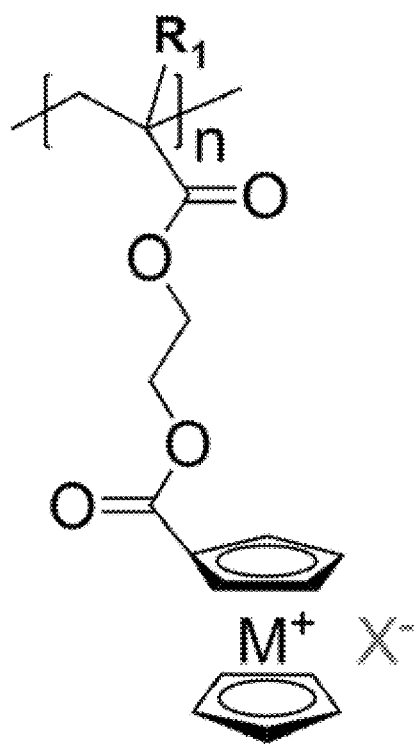
FIG. 2A shows an exemplary anion-paired metallocene-containing homopolymer (poly(2-(methacrylolyoxy) ethyl metalloceniumcarboxylate)), where M is a metal and X is an anion.
Figure 2B:
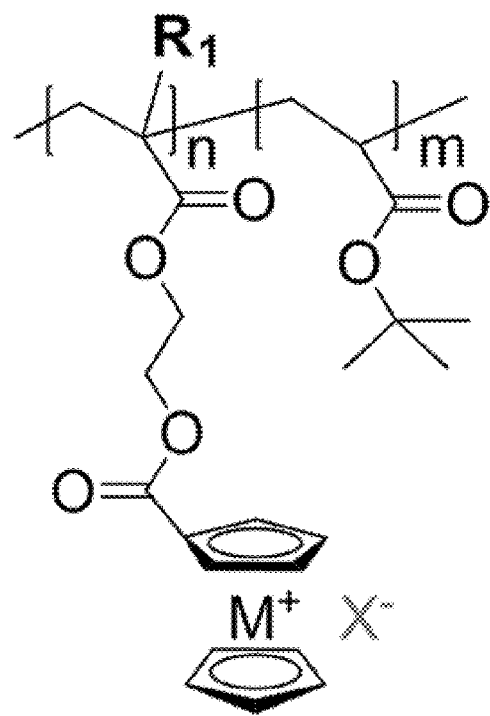
FIG. 2B shows an exemplary anion-paired metallocene-containing diblock copolymer paired with anions with poly(tert-butyl acrylate) as the other block, where M is a metal and X is an anion.
Figure 2C:
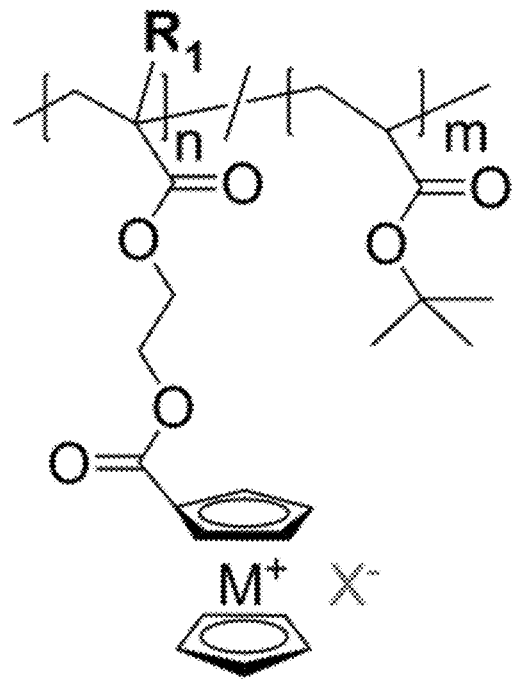
FIG. 2C shows an exemplary anion-paired metallocene-containing random copolymer with tert-butyl acrylate as a co-monomer, where M is a metal and X is an anion.

For example, referring to FIG. 2A, the anion-paired metallocene-containing monomer 10 of FIG. 1B is shown after polymerization into a homopolymer, where n is the number of repeating monomeric units of the anion-paired metallocene-containing monomer 10. Alternatively, FIG. 2B shows the anion-paired metallocene-containing monomer 10 of FIG. 1B after polymerization into a block copolymer with poly(tert-butyl acrylate) as the other block, where n is the number of repeating monomeric units of the anion-paired metallocene-containing monomer 10 and m is the number of repeating monomeric units of the tert-butyl acrylate monomer. Finally, FIG. 2C shows the anion-paired metallocene-containing monomer 10 of FIG. 1B after polymerization into a random copolymer with poly(tert-butyl acrylate) as the other comonomer, where n is the number of monomeric units of the anion-paired metallocene-containing monomer 10 and m is the number of monomeric units of the tert-butyl acrylate monomer within the polymer. In one embodiment, n is about 5 to about 1000. Similarly, m can be about 5 to about 1000. In particular embodiments, the polymer molecular weight is in the range of 1,000 g/mol to 1,000,000 g/mol.

The properties of the anion-paired metallocene-containing polymers can be tuned by changing the monomer structures (the polymerizable vinyl moiety, the linker or the anion-paired metallocene-containing moiety), the molecular weight of the polymer, the compositions of various comonomers, and/or the relative amounts of any comonomers present.

III. Anion-Paired Metallocene-Containing Compounds and Polymers

The use of cationic metallocene-containing compounds and polymers has been found to be antimicrobial agents, particularly when the anion paired with the cationic metallocene-containing compounds and polymers is $F^-$, $Cl^-$, $Br^-$, or $I^-$. For example, cobaltocenium-containing polymers with $F^-$, $Cl^-$, $Br^-$ and $I^-$ anions have antimicrobial activities against a broad spectrum of bacteria, including methicillin-sensitive *Staphylococcus aureus* (MSSA) and many kinds of drug resistance *Staphylococcus aureus* (MRSA) (community-associated (CA-MRSA), hospital-associated (HA-MRSA) and MRSA-252).

Such compounds can be administered in a pharmaceutically effective amount as an antibiotic to a subject (e.g., a human) infected with such bacteria (i.e., an cationic metallocene-containing antibiotic). The cationic metallocene-containing antibiotic may be administered into the subject via any suitable routes of administration, such as oral, rectal, transmucosal, transnasal, intestinal, or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Pharmaceutical compositions that include the cationic metallocene-containing antibiotic may be manufactured by processes well known in the art, e.g., by means of conventional mixing, dissolving, granulating, dragee-making, levigating, emulsifying, encapsulating, entrapping or lyophilizing processes. Thus, such pharmaceutical compositions comprising the cationic metallocene-containing antibiotic may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, artificial CSF or physiological salt buffer. For transmucosal administration, penetrants appropriate to the barrier to be permeated are used in the formulation. Such penetrants are generally known in the art. For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Determination of a therapeutically effective amount is well within the capability of those skilled in the art, especially in light of the detailed disclosure provided herein. Toxicity and therapeutic efficacy of the cationic metallocene-containing antibiotic described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition.

Depending on the severity and responsiveness of the condition to be treated, dosing can be of a single or a plurality of administrations, with course of treatment lasting from several days to several weeks or until cure is effected or diminution of the infected state is achieved.

The amount of a cationic metallocene-containing antibiotic to be administered will, of course, be dependent on the subject being treated, the severity of the affliction, the manner of administration, the judgment of the prescribing physician, etc.

IV. Antibiotic-Loaded Metallocene-Containing Compounds and Polymers

In one embodiment, the cationic metallocene derivatives can be used to promote the effects of traditional antibiotics against a broad spectrum of bacterial pathogens including drug resistant bacteria. Cationic metallocene compounds and polymers have at least one positive charged metallocene unit. In such cationic metallocene derivatives, the anion (X) as shown in FIGS. 1 and 2, is replaced with an anionic antibiotic compound. Thus, the cationic metallocene-containing moiety is paired with an anionic antibiotic compound.

All β-lactam type antibiotics, such as penicillins, carbapenems and cephalosporins (including the first, second, third, fourth and fifth generation), are able to be loaded in cationic metallocene molecules and polymers. These antibiotics loaded cationic metallocene-containing compounds have excellent effects against Gram-negative and Gram-positive bacteria, including various kinds of multidrug-resistant *Staphylococcus aureus* (MRSA).

Thus, traditional antibiotics can be loaded in cationic metallocene-containing materials and can have antimicrobial activities against a broad spectrum of drug resistant bacterial pathogens. Exemplary antibiotics that can be paired with the cationic metallocene-containing compounds, include but are not limited to, penicillins (Penams): Amoxicillin, Ampicillin (Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam Sulbenicillin, Clometocillin, Benzathine, benzylpenicillin, Procaine benzylpenicillin, Azidocillin, Penamecillin, Phenoxymethylpenicillin (V), Propicillin, Benzathine phenoxymethylpenicillin and Pheneticillin; cephalosporins, including the first, second, third, fourth and fifth generation of them; carbapenems, including Biapenem, Ertapenem, Doripenem, Imipenem, Meropenem and Panipenem; etc.

Figure 6B:
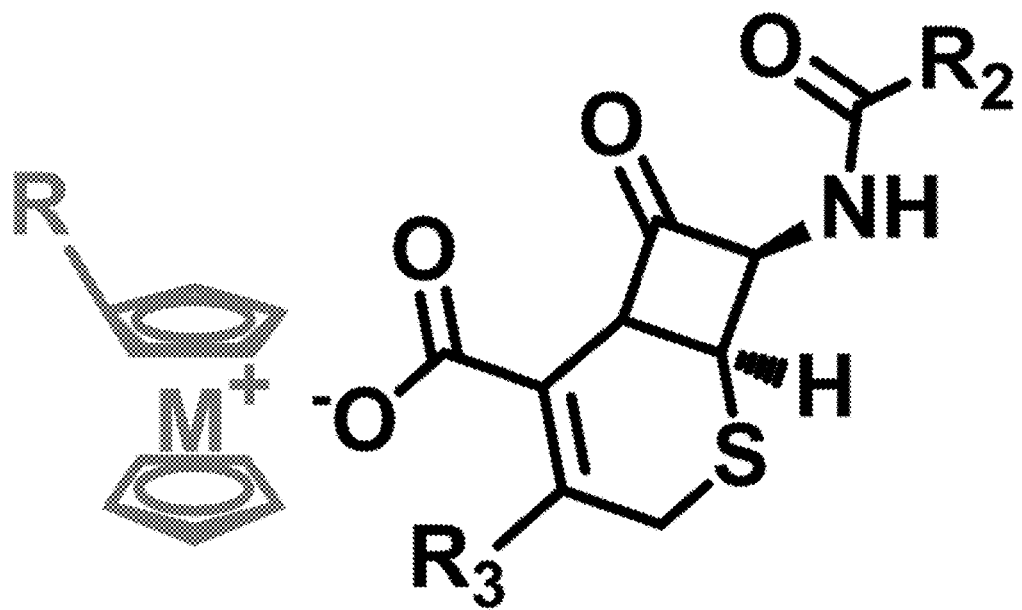
FIG. 6B shows an antibiotic-loaded metallocene-containing compound or polymer, with the anti-biotic shown as a cephalosporin or related compound, where M is a metal, R is a linker on metallocene (e.g., small molecule linkers, oligomer linkers and polymer linkers), and $R_2$ and $R_3$ represent a functional group of the antibiotic (e.g., an organic functional group).
Figure 6C:
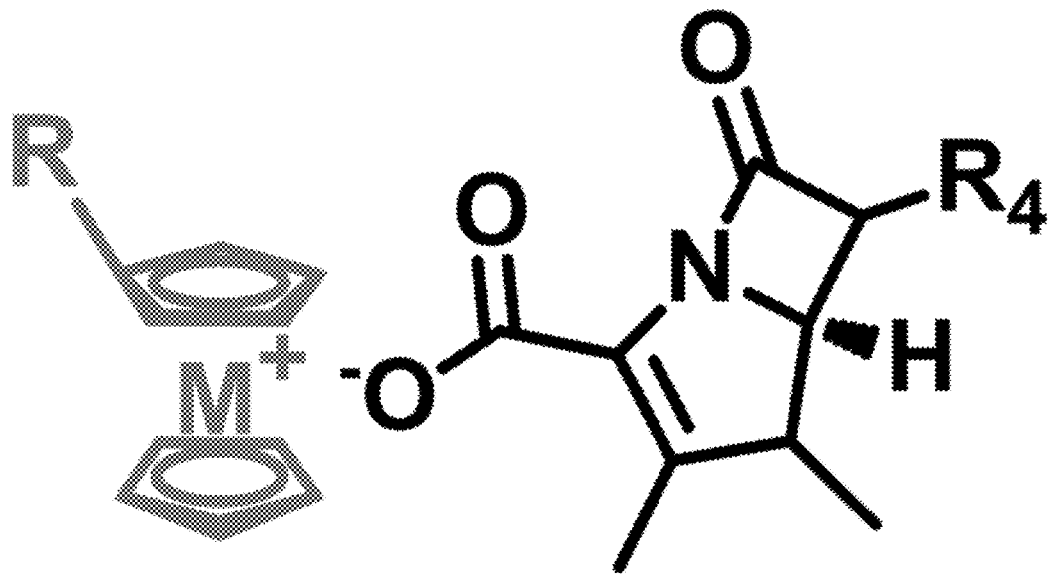
FIG. 6C shows an antibiotic-loaded metallocene-containing compound or polymer, with the anti-biotic shown as a carbapenem or related compound, where M is a metal, R is a linker on metallocene (e.g., small molecule linkers, oligomer linkers and polymer linkers), and $R_4$ represents a functional group of the antibiotic (e.g., an organic functional group).

For example, FIG. 6A shows an antibiotic-loaded metallocene-containing compound, with the anti-biotic shown as a penicillin or related compound, where M is a metal, R is a linker on metallocene (e.g., small molecule linkers, oligomer linkers and polymer linkers), and $R_1$ represents a functional group of the antibiotic (e.g., an organic functional group). In another exemplary embodiment, FIG. 6B shows an antibiotic-loaded metallocene-containing compound or polymer, with the anti-biotic shown as a cephalosporin or related compound, where M is a metal, R is a linker on metallocene (e.g., small molecule linkers, oligomer linkers and polymer linkers), and $R_2$ and $R_3$ represent a functional group of the antibiotic (e.g., an organic functional group). In still a further exemplary embodiment, FIG. 6C shows an antibiotic-loaded metallocene-containing compound or polymer, with the anti-biotic shown as a carbapenem or related compound, where M is a metal, R is a linker on metallocene (e.g., small molecule linkers, oligomer linkers and polymer linkers), and $R_4$ represents a functional group of the antibiotic (e.g., an organic functional group).

Figure 7:
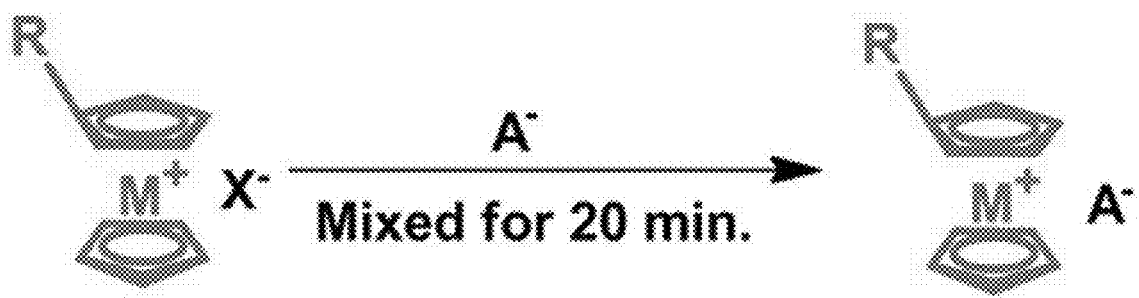
FIG. 7 shows a loading mechanism for an exemplary anionic antibiotic (represented by A), where M is a metal, $X^-$ is an anion, and R is a linker on metallocene.
Figure 8A:
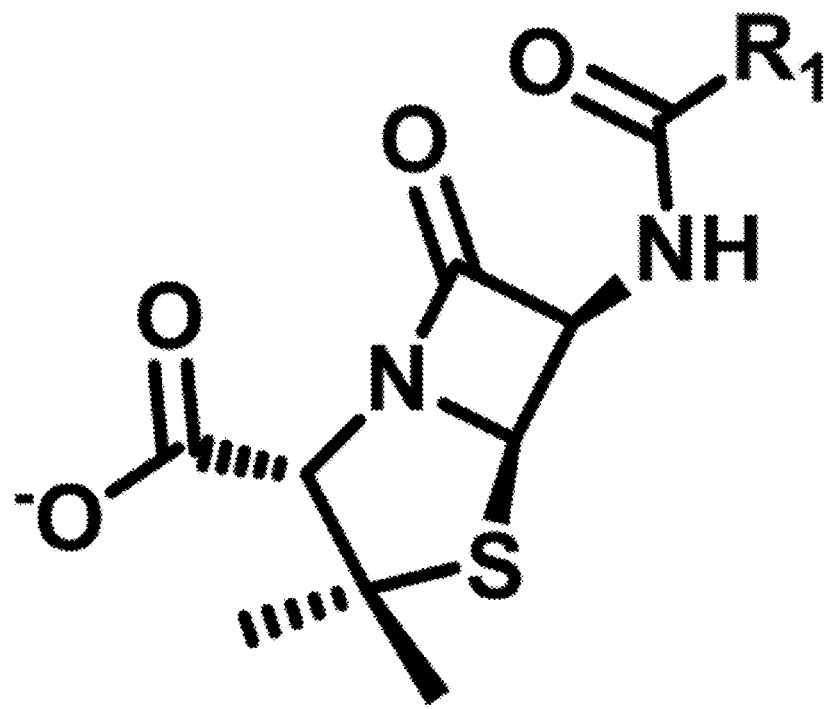
FIG. 8A shows a penicillin as the exemplary anionic antibiotic A in FIG. 7, where $R_1$ represent a functional group of the antibiotic (e.g., an organic functional group).
Figure 8B:
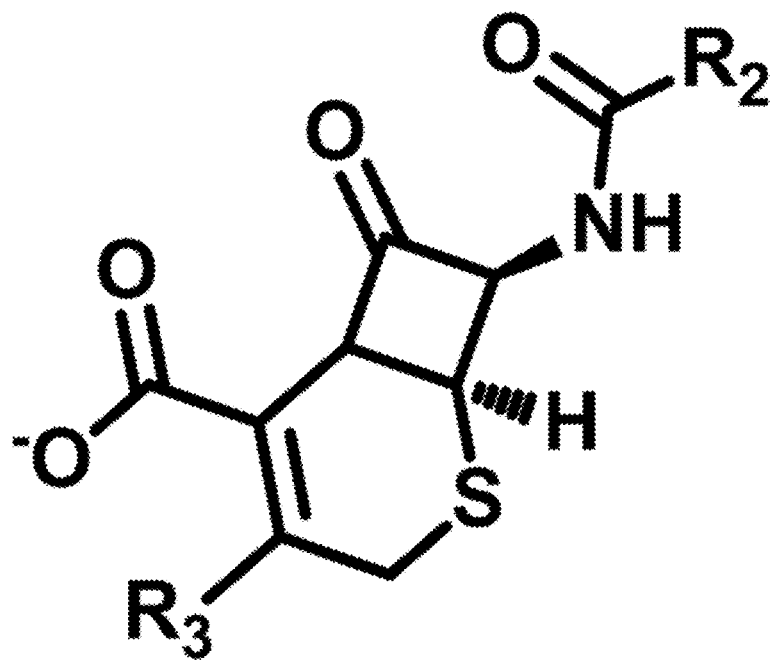
FIG. 8B shows a cephalosporin as the exemplary anionic antibiotic A in FIG. 7, where $R_2$ and $R_3$ represent a functional group of the antibiotic (e.g., an organic functional group).
Figure 8C:
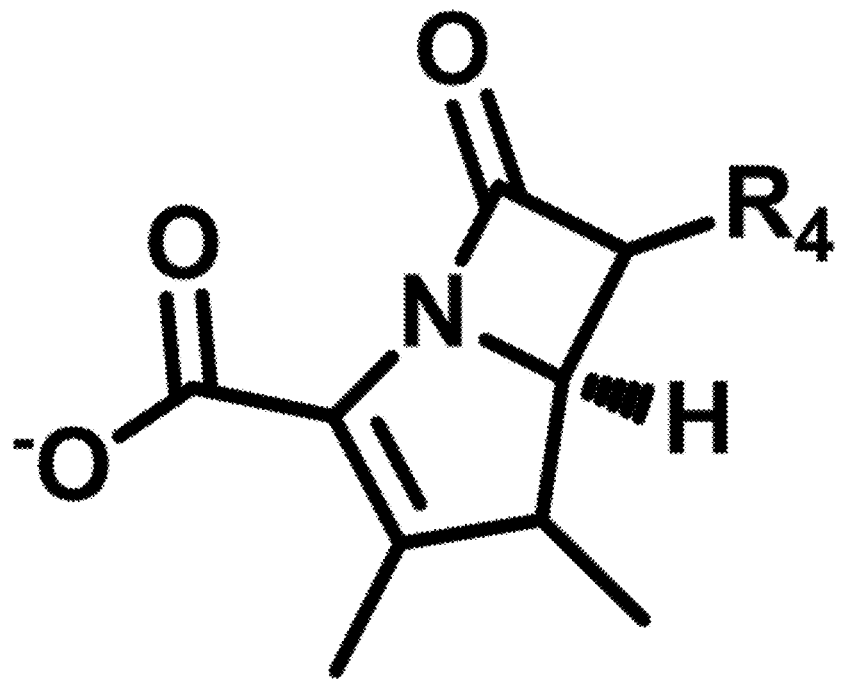
FIG. 8C shows a carbapenem as the exemplary anionic antibiotic A in FIG. 7, where $R_4$ represent a functional group of the antibiotic (e.g., an organic functional group).

FIG. 7 shows a loading mechanism for an exemplary antibiotic (represented by A) into the exemplary anion-paired metallocene-containing compound of FIG. 1A, where M is a metal, $X^-$ is an anion, and R is a linker on metallocene (e.g., an organic group forming a monomer or polymer as shown in FIGS. 1 and 2). For example, A can be an anionic penicillin (as shown in FIG. 8A, where $R_1$ represent a functional group of the antibiotic); an anionic cephalosporin (as shown in FIG. 8B, where $R_2$ and $R_3$ represent a functional group of the antibiotic); an anionic carbapenem (as shown in FIG. 8C, where $R_4$ represent a functional group of the antibiotic), or the like.

Thus, completely new methods and compounds in biomedical applications are provided. The implementation of cationic metallocene-containing compounds and polymers greatly enhances the effects of traditional antibiotics against abroad spectrum of bacterial pathogens, especially drug resistant bacteria.

EXAMPLES

The utilization of different anion-paired cationic metallocene-containing compounds, homopolymers, block copolymers, graft copolymers, star copolymers or organic/inorganic hybrids as new antimicrobial materials was demonstrated. Different anions (including, but not limited to, $PF_6^-$, $OTf^-$, $BPh_4^-$, $BF_4^-$, $F^-$, $Cl^-$, $Br^-$, $I^-$, $NO_3^-$, $Ac^-$, $SO_4^{2-}$, $HSO_4^-$, $ClO_4^-$, $BrO_3^-$, $CN^-$, $SCN^-$, $OH^-$, $H_2PO_4^-$ and $HCOO^-$) were paired with cationic metallocene-containing polymers.

The use of cationic metallocene-containing compounds and polymers was demonstrated as excellent antimicrobial agents. For example, cobaltocenium-containing polymers with $F^-$, $Cl^-$, $Br^-$ and $I^-$ anions show antimicrobial activities against a broad spectrum of bacteria, including methicillin-sensitive *Staphylococcus aureus* (MSSA) and many kinds of drug resistance *Staphylococcus aureus* (MRSA) (community-associated (CA-MRSA), hospital-associated (HA-MRSA) and MRSA-252).

Example 1

Figure 3:
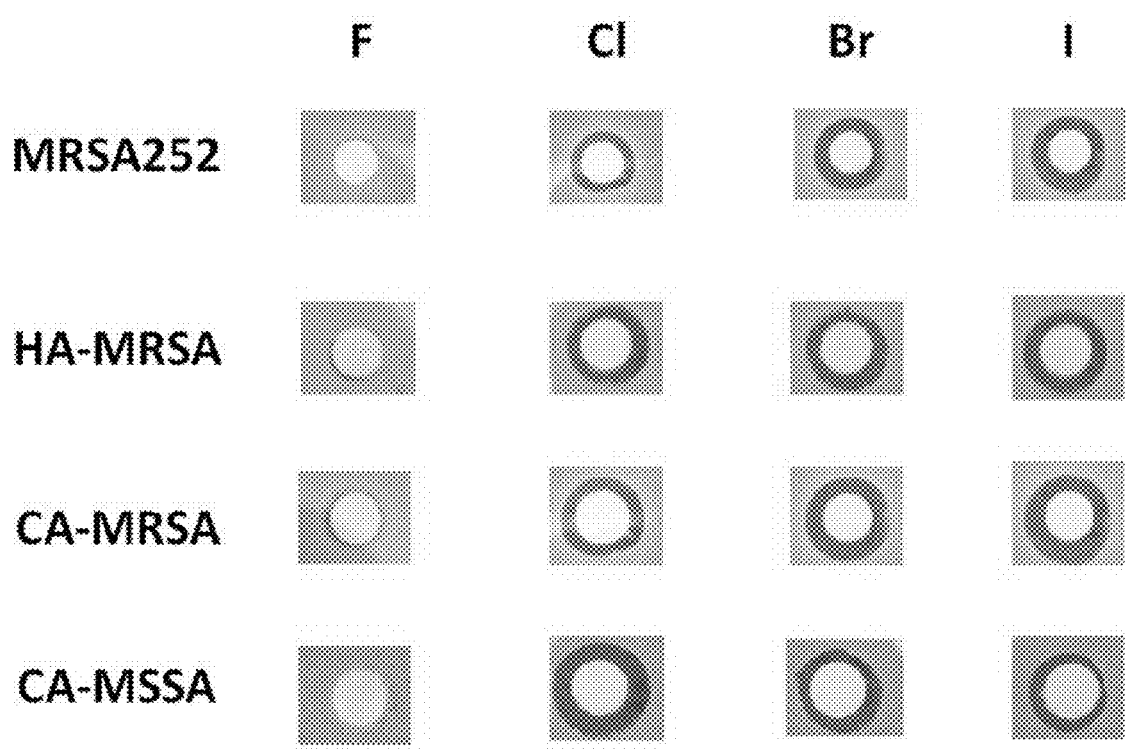
FIG. 3 shows an Agar diffusion method to test antimicrobial activity of $F^-$, $Cl^-$, $Br^-$ and $I^-$ paired cationic cobaltocenium-containing polymers (at 10 μM for HA-MRSA, CA-MRSA and CA-MSSA, 15 μM for MRSA-252) against strains of methicillin-resistant *Staphylococcus aureus* (MRSA-252, HA-MRSA, CA-MRSA and CA-MSSA).
Figure 4:
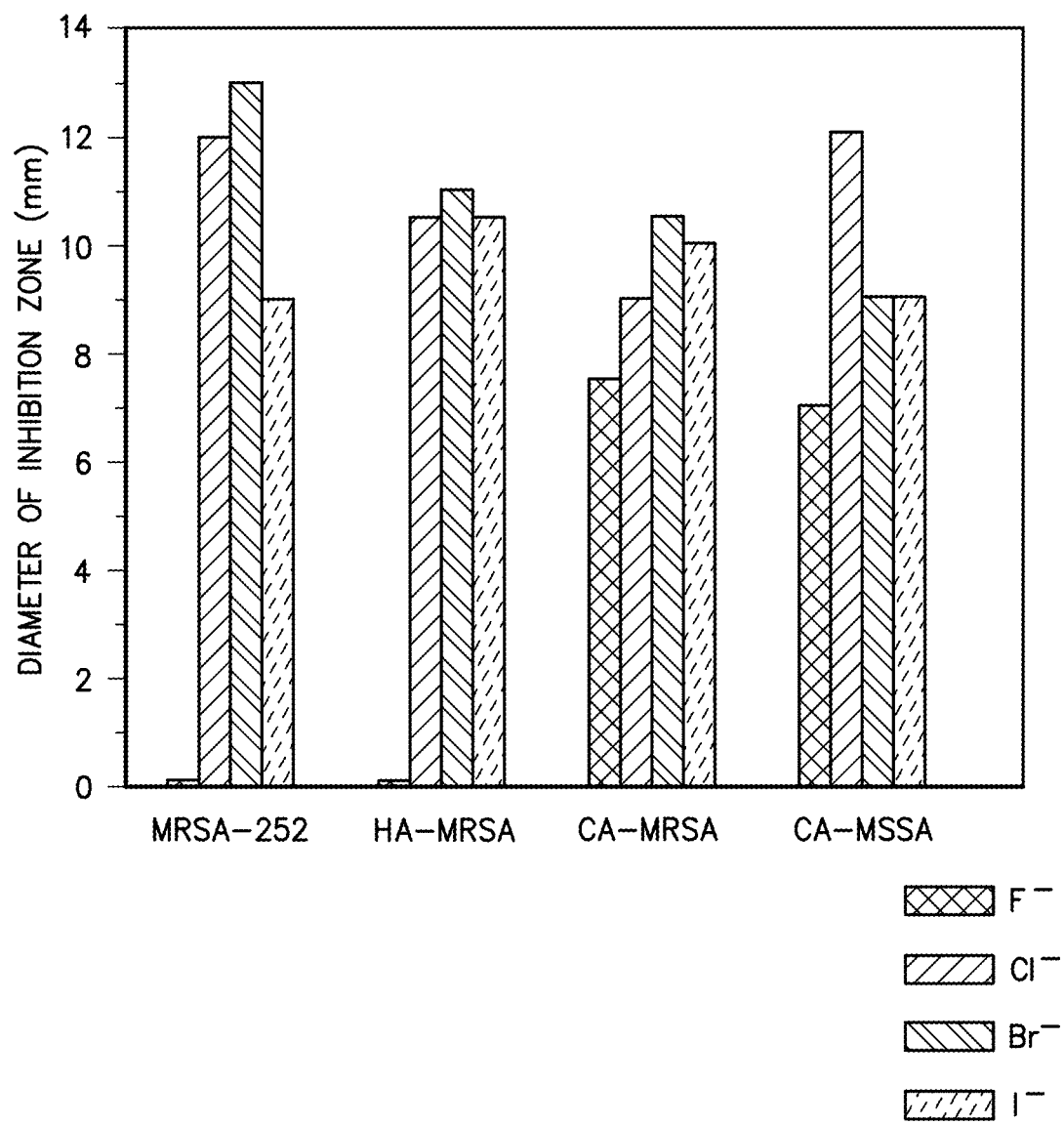
FIG. 4 shows the size (diameter, mm) of inhibition zones after incubation of bacterial (MRSA-252, HA-MRSA, CA-MRSA and CA-MSSA) with different anions ($F^-$, $Cl^-$, $Br^-$ and $I^-$) paired methacrylate cobaltocenium-containing polymers (at 10 μM for HA-MRSA, CA-MRSA and CA-MSSA, 15 μM for MRSA-252).

This example demonstrates that cationic metallocene-containing polymers can be used as antimicrobial agents towards MRSA-252, HA-MRSA, CA-MRSA and CA-MSSA. Cationic cobaltocenium-containing polymers with $F^-$, $Cl^-$, $Br^-$ and $I^-$ as anions ($M_n$=16390 g/mol for $F^-$-associated polymer, 17000 g/mol (for $Cl^-$), 19000 g/mol (for $Br^-$), 21100 g/mol (for $I^-$), $M_w/M_n$=1.25). All bacterial cells are incubated in tryptic soy broth (TSB, 30 g/L) media under 37° C. for 24 hours. Fifteen milliliters of the sterilized melted agar medium is left to solidify on agar plates at room temperature, and then 1 mL of bacterial cell suspensions containing $10^5$ cells/mL are evenly distributed over the surface of the agar plates. Then 6 mm filter discs are added to the plate surface, and 30 μL $F^-$, $Cl^-$, $Br^-$ and $I^-$ paired cobaltocenium-containing polymers solutions (10 μM, in water) are added to each disc (for MRSA-252 cells, 15 μM solution was used). FIG. 3 and FIG. 4 show the inhibition ds different bacterial cells by this disk diffusion method (ASTM: the Kirby Bauer diffusion test). FIG. 5 (SEM image) further demonstrates the lysis of HA-MRSA cell membranes by iodide-paired cationic cobaltocenium-containing homopolymers.

Example 2

The utilization of cationic metallocene-containing compounds, homopolymers, block copolymers, graft copolymers, star copolymers or organic/inorganic hybrids as drug delivery materials for traditional antibiotics was demonstrated. Different commercial available antibiotics (including all β-lactam type antibiotics, such as penicillins, carbapenems and cephalosporins (including the first, second, third, fourth and fifth generation) were loaded with cationic metallocene-containing polymers. FIG. 7 shows the loading mechanism for these exemplary antibiotics.

The utilization of cationic metallocene-containing compounds and polymers to activate conventional antibiotics against drug-resistant bacterial pathogens was demonstrated. For example, cobaltocenium-containing polymers loaded with penicillin G show antimicrobial activities against a broad spectrum of bacteria, including many kinds of MRSA (CA-MRSA, HA-MRSA and MRSA-252).

This example demonstrates that traditional antibiotics loaded in cationic metallocene-containing polymers could have strong effects against drug resistant bacterial pathogens, including MRSA-252 and CA-MRSA. Penicillin G (benzyl penicillin) was loaded in cationic cobaltocenium-containing polymers by mixing them for 20 minutes. The counterion anion exchange results in the loading of antibiotics in polymer matrix. Cationic cobaltocenium-containing polymers can be synthesized according to Zhang, J. Y., Ren, L. X., Hardy, C. G., Tang, C. B., Cobaltocenium-Containing Methacrylate Homopolymers, Block Copolymers, and Heterobimetallic Polymers via RAFT Polymerization. *Macromolecules* 45, 6857 (2012).

Figure 9:
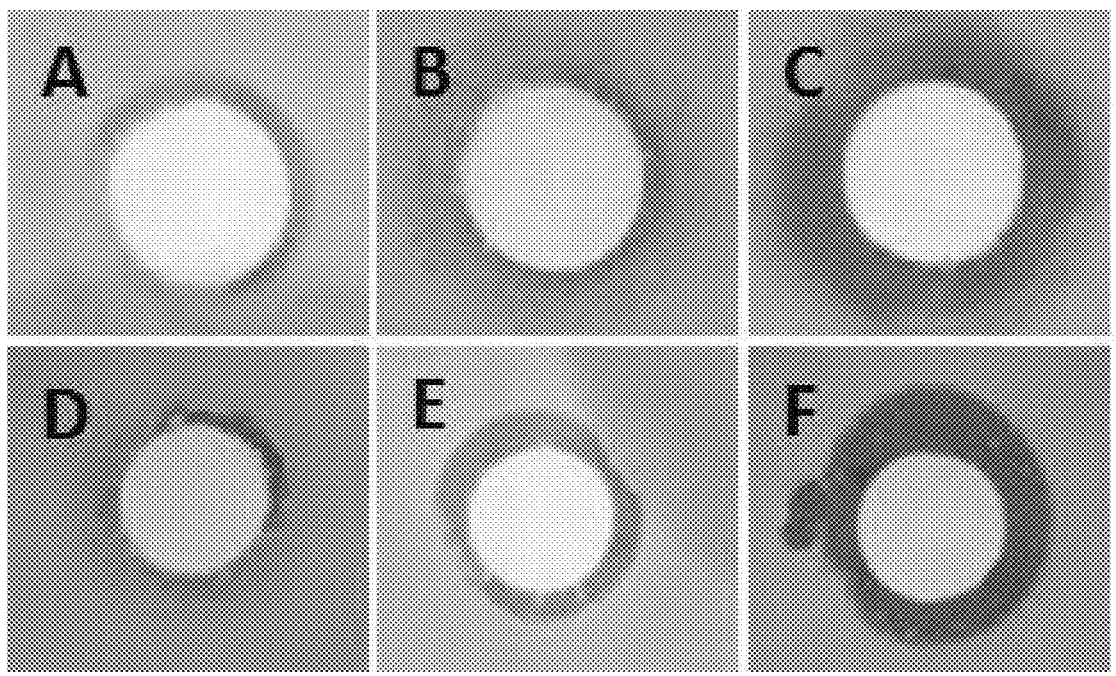
FIG. 9 shows an Agar diffusion method to test antimicrobial activity of cationic cobaltocenium-containing polymers, penicillin G; penicillin G loaded polymer against MRSA. For CA-MRSA, box (A) shows the activity with 37 μg polymer, box (B) shows the activity with 6 μg penicillin G, box (C) shows the activity with 37 μg polymer loaded with 6 μg penicillin G. For MRSA-252, box (D) shows the activity with 37 μg polymer, box (E) shows the activity with 8 μg penicillin G, and box (F) shows the activity with 37 μg polymer loaded with 8 μg penicillin G.

All bacterial cells were incubated in tryptic soy broth (TSB, 30 g/L) media under 37° C. for 24 hours. Fifteen milliliters of the sterilized melted agar medium was left to solidify on agar plates at room temperature, and then 1 mL of bacterial cell suspensions containing $10^5$ cells/mL were evenly distributed over the surface of the agar plates. Then 6 mm filter discs were added to the plate surface, and 10 μL solutions of penicillin G and cobaltocenium-containing polymers (concentration for CA-MRSA: 3.7 μg/mL of polymer and 0.6 μg/ml penicillin, in water; for MRSA-252, 3.7 μg/mL of polymer and 0.8 μg/ml penicillin) were added to each disc. FIG. 9 shows the enhanced efficacy of penicillin G via cationic cobaltocenium-containing polymers against CA-MRSA and MRSA-252 cells.

Figure 10:
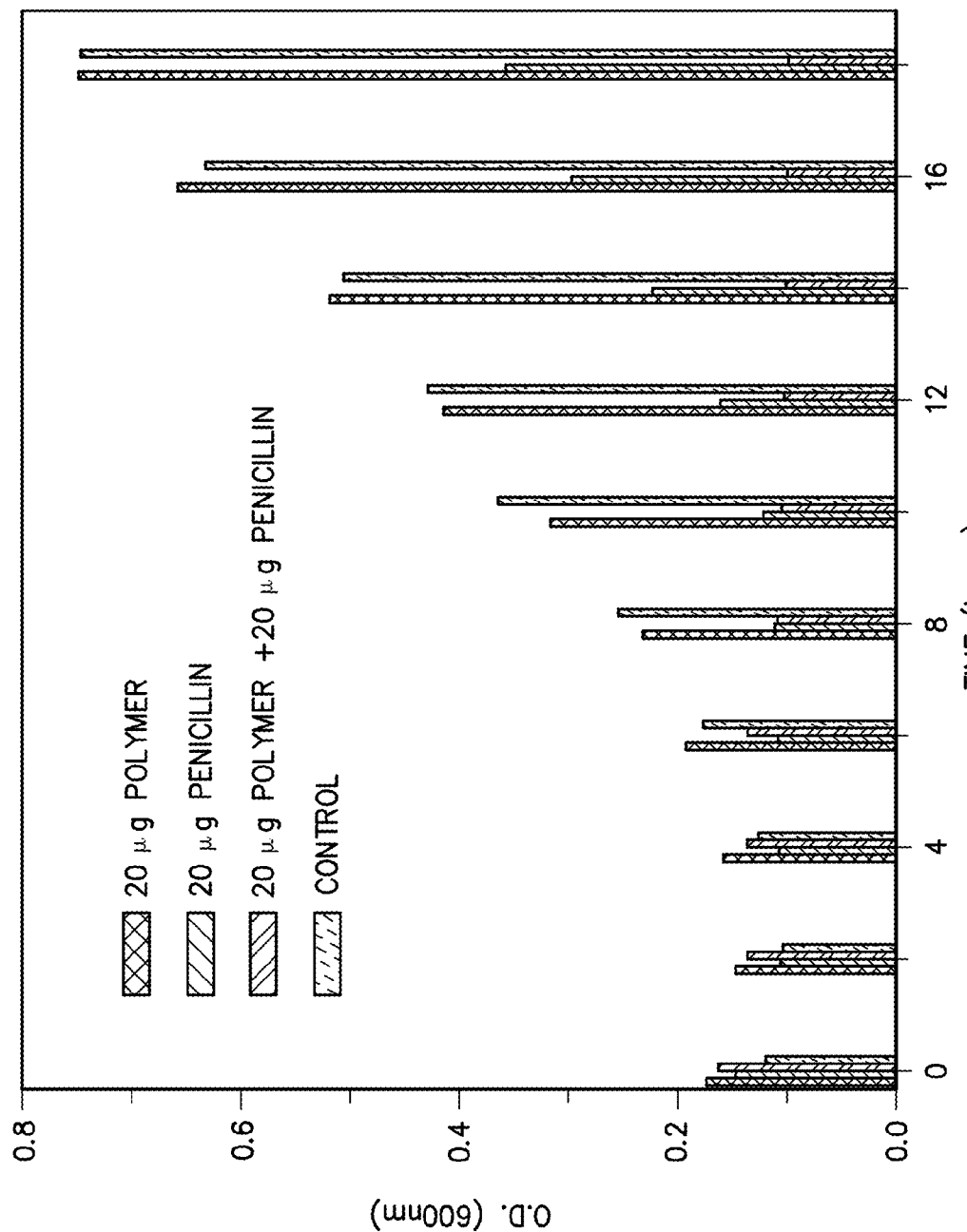
FIG. 10 shows results of a Broth dilution method to test antimicrobial activity of cationic cobaltocenium-containing polymers, penicillin G and penicillin loaded polymer against CA-MRSA.

Broth dilution method was used to characterize the inhibition of penicillin G/polymer complex against CA-MRSA cells. Penicillin G, cationic cobaltocenium polymer or penicillin G/polymer complex was dissolved in water. Concentrations of the above solutions were at 20 μg/ml for penicillin G, 20 μg/ml for cationic polymer and 40 μg/ml penicillin G loaded polymer (20 μg/ml penicillin G and 20 μg/ml polymer). Solutions without polymers were prepared as the control samples. CA-MRSA cells were grown in tryptic soy broth (TSB) medium at 37° C. overnight. All bacteria were grown to an optical density of 1 ($OD_{600}$=1). Then, the cells were diluted with TSB to give a bacterial assay stock with $OD_{600}$=0.04. CA-MRSA cells (90 mL) were added to each well in a 96 well assay plate. 1 mL of three stock solutions (penicillin G, polymer and penicillin loaded polymer were then added to the wells. The assay was incubated at 37° C. for 12 hours. Bacterial growth is detected every 2 hours at $OD_{600}$ and is compared with controls of TSB without polymers and bacterial strains. All assays are carried out in duplicate in the same assay plate. According to FIG. 10, for cationic polymer, it showed no inhibition towards CA-MRSA cells. While for penicillin G, some inhibition against CA-MRSA was observed. However, for penicillin loaded polymers, strong inhibition against CA-MRSA was observed during 16 hours.

Thus, this work shows the utilization of cationic metallocene-containing compounds and polymers to enhance the inhibition effects of conventional antibiotics against a broad spectrum of bacterial cells, including Gram-negative and Gram-positive bacteria, such as various kinds of methicillin-resistant *Staphylococcus aureus* (MRSA).

Example 3

A class of charged metallopolymers are introduced, which not only show high efficacy in reducing β-lactamase activity, but also effectively lyse bacterial cells. The results reveal that these metallopolymers attack both β-lactamase enzymes and cell walls, and protect conjugated antibiotics via ion-pairing between polymers and antibiotics. (See, FIGS. 11A-11C). Specifically, these charged metallopolymers are based on cationic cobaltocenium-containing polymers. Due to the unique ability of cationic cobaltocenium moieties to complex with carboxylate anions, various commercial β-lactam antibiotics, including penicillin-G, amoxicillin, ampicillin and cefazolin, can be protected from β-lactamase via the formation of stable ion-pairs with cationic cobaltocenium-containing polymers. Considering these synergistic attributes, these metallopolymers show high efficiency against multidrug-resistant MRSA, while exhibiting non-hemolytic activity and minimal in vitro and in vivo toxicity.

Hexafluorophosphate ($PF_6^-$)-paired cobaltocenium-containing polymers, poly(2-(methacrylolyoxy)ethyl cobaltoceniumcarboxylate hexafluorophosphate) ($M_n$=15,600 g/mol, $M_w/M_n$=1.25), was prepared and used for this study. Halide anion- ($Cl^-$, $Br^-$ and $I^-$) paired cationic cobaltocenium polymers were subsequently prepared. All halide-paired polymers are hydrophilic and highly soluble in water (solubility>800 mg/mL).

β-Lactamase production and excretion is a major defense mechanism employed by several drug-resistant bacterial pathogens, such as various strains of MRSA. Effects of cationic cobaltocenium-containing polymers on β-lactamase activity were conducted by incubation of (β-lactamase (obtained from HA-MRSA (ATCC 29213) extracellular solution) with nitrocefin and halide-paired cobaltocenium-containing polymers together. Nitrocefin is a chromogenic cephalosporin that is classified as a β-lactam antibiotic and is typically used to indicate the existence of β-lactamase. A solution of nitrocefin with a pristine β-lactam ring typically appears yellow with an absorption peak near 380 nm. However, after hydrolysis of the β-lactam ring by β-lactamase, the solution typically turns red with an absorption peak near 480 nm (the control sample). As shown in FIG.

Figure 12A:
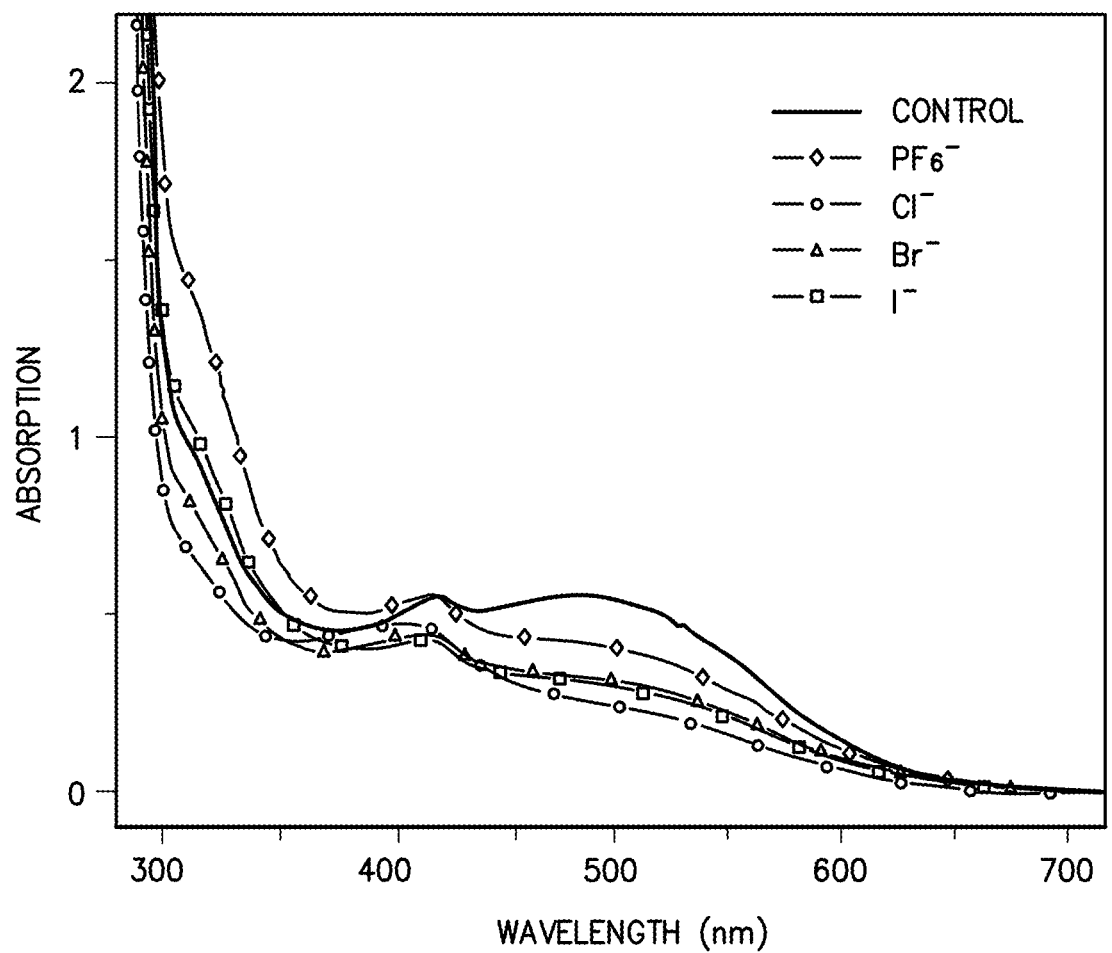
FIG. 12A shows the UV-vis absorption of a nitrocefin solution with 5 μM anion-paired metallopolymers and β-lactamase incubated for 3 hours.
Figure 12B:
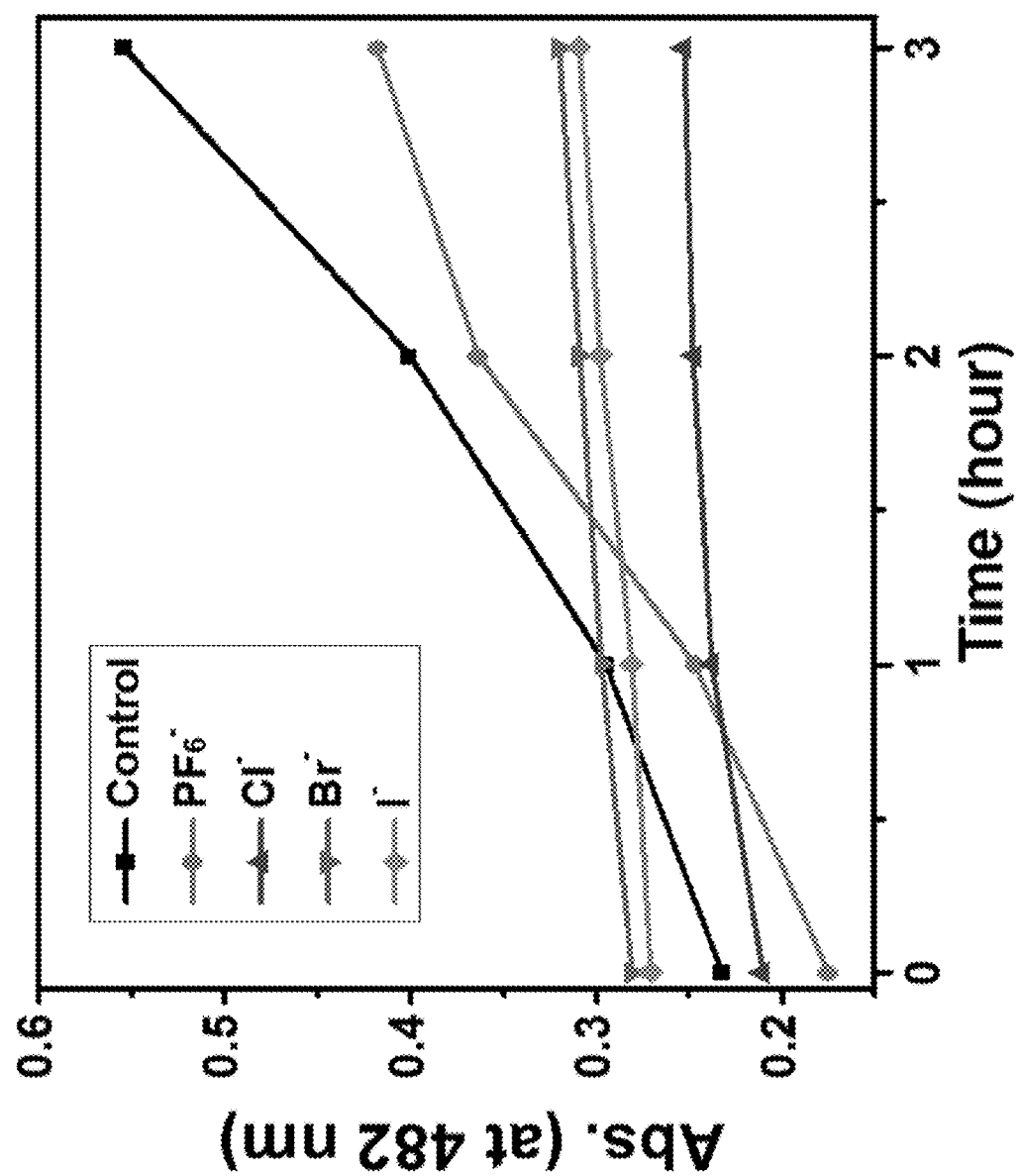
FIG. 12B shows the incubation time-dependent absorption (at 482 nm) of nitrocefin solution with different anion-paired metallopolymers at 5 μM and β-lactamase.
Figure 12C:
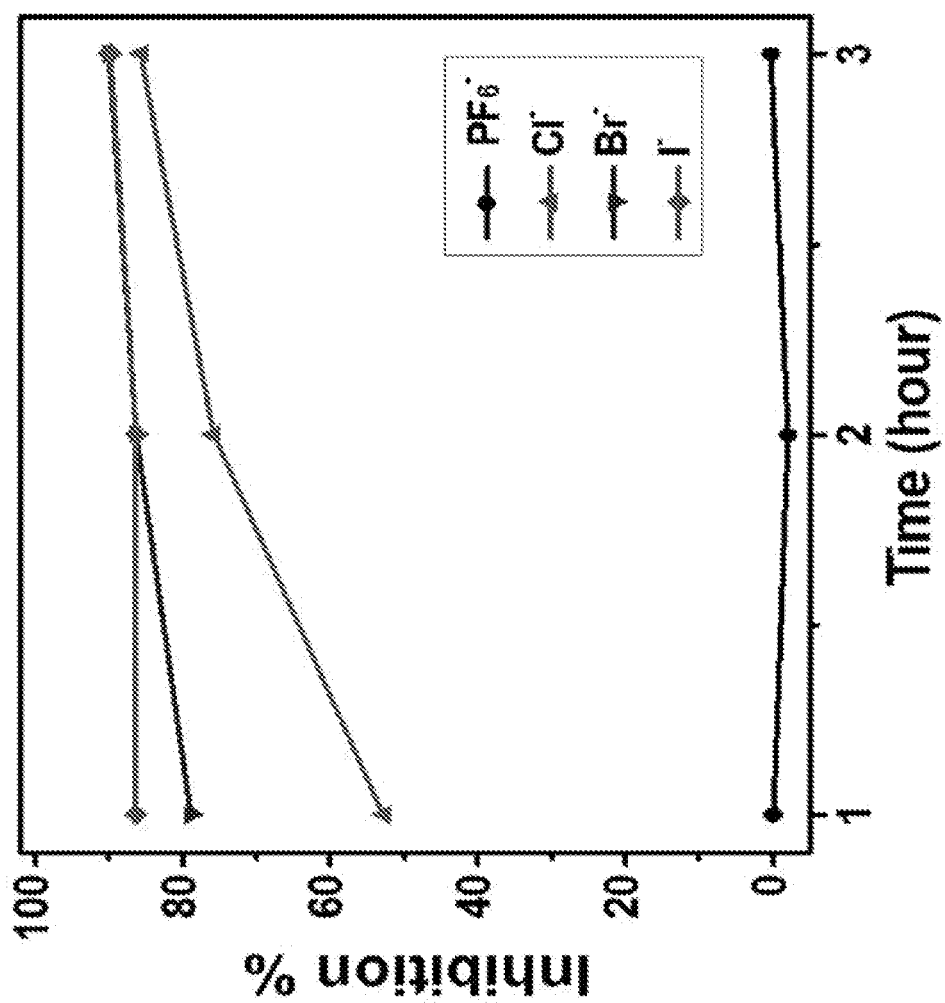
FIG. 12C shows the level of β-lactamase activity inhibition by different anion-paired cationic cobaltocenium-containing polymers at 5 μM.

12A, incubation of β-lactamase with halide-paired polymers and nitrocefin resulted in little hydrolysis (solutions remained yellow with low absorption at 482 nm), although those with $PF_6^-$-paired polymers resulted in significant hydrolysis of nitrocefin (the solution turned red with high absorption at 482 nm). A time-dependent study was conducted by measuring absorption at 482 nm at different time intervals (FIG. 12B). The inhibition of β-lactamase is shown in FIG. 1d. More than 80% inhibition of β-lactamase activity was achieved by metallopolymers at 5 μM. The use of metallopolymers at 10 μM shut down the β-lactamase hydrolysis completely. However, negligible inhibition of β-lactamase was observed for $PF_6^-$-paired metallopolymer, possibly due to its poor solubility in water.

Figure 13A:
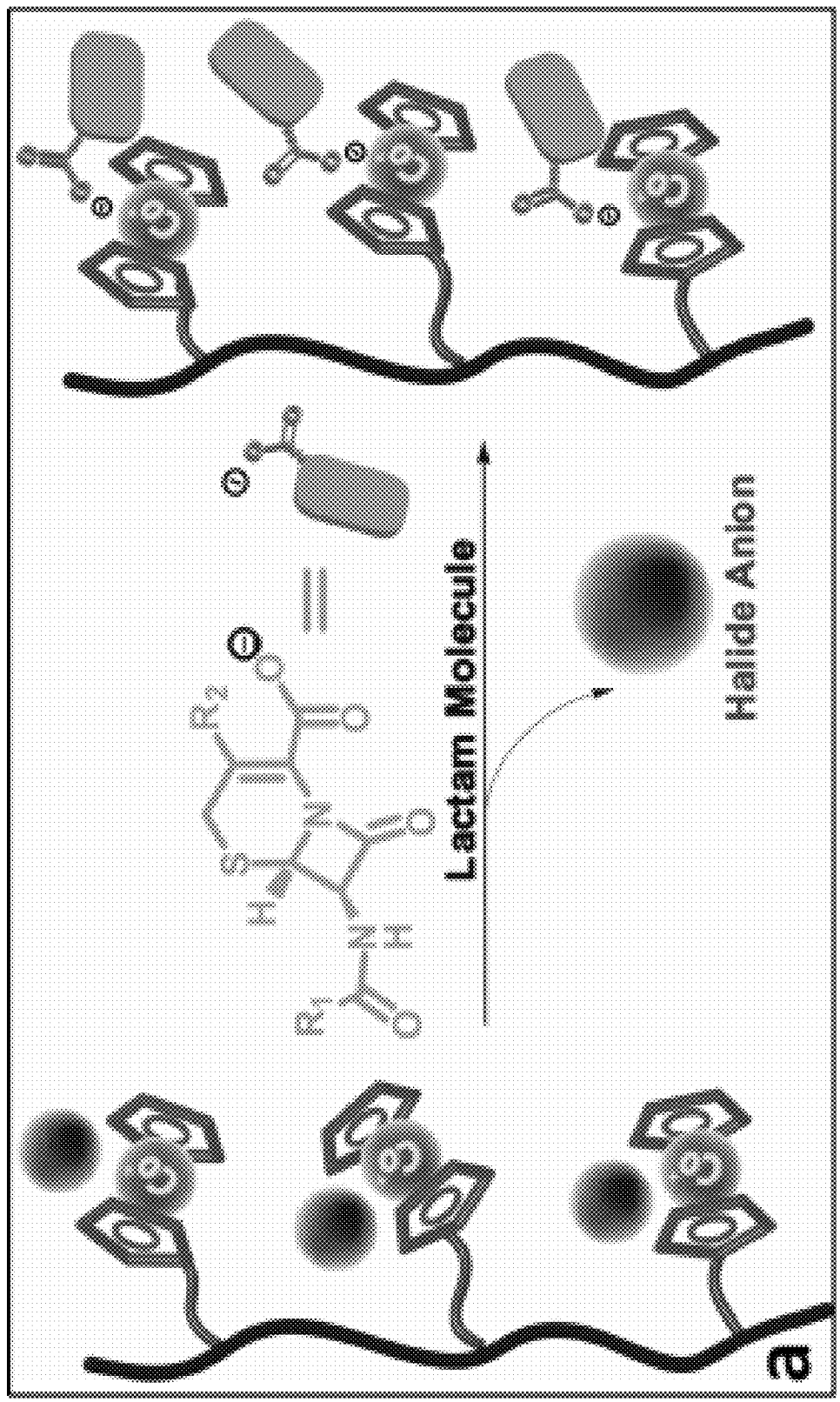
FIG. 13A shows a schematic of the formation of ion-pairs between β-lactam antibiotics and cationic cobaltocenium-containing polymers.
Figure 13B:
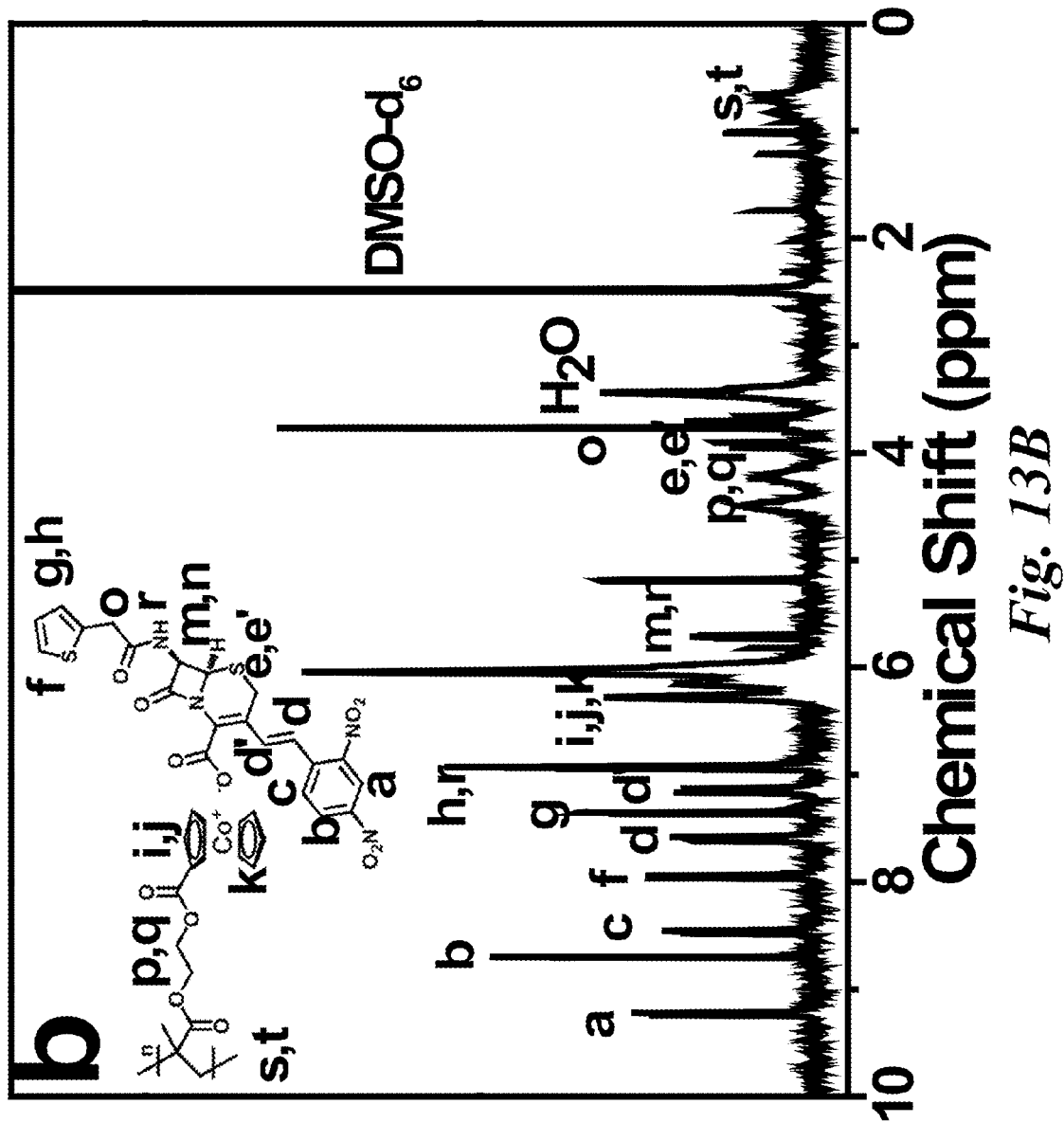
FIG. 13B shows $^1H$ NMR spectrum for ion-pairs of nitrocefin and cationic cobaltocenium-containing polymers.

The protection of nitrocefin by metallopolymers may be due to the unique ability of cationic cobaltocenium moieties to form ion-pairs with the carboxylate anion in nitrocefin. Carboxylate anions in nitrocefin could readily perform counter-ion exchange with halide counter-ions in these cobaltocenium-containing polymers, leading to the formation of nitrocefin-metallopolymer conjugates with 1:1 pairing between nitrocefin and cobaltocenium moieties (FIGS. 13A and 13B). Preliminary studies indicated that such ion-pairing interaction may block the electrostatic anchoring by amino acid residue ($Lys_{234}$) and could also prevent the key acylation and deacylation steps from $Glu_{166}$ in β-lactamases produced by MRSA. However, detailed mechanisms are still under study.

Figures 11A, 11B, 11C:
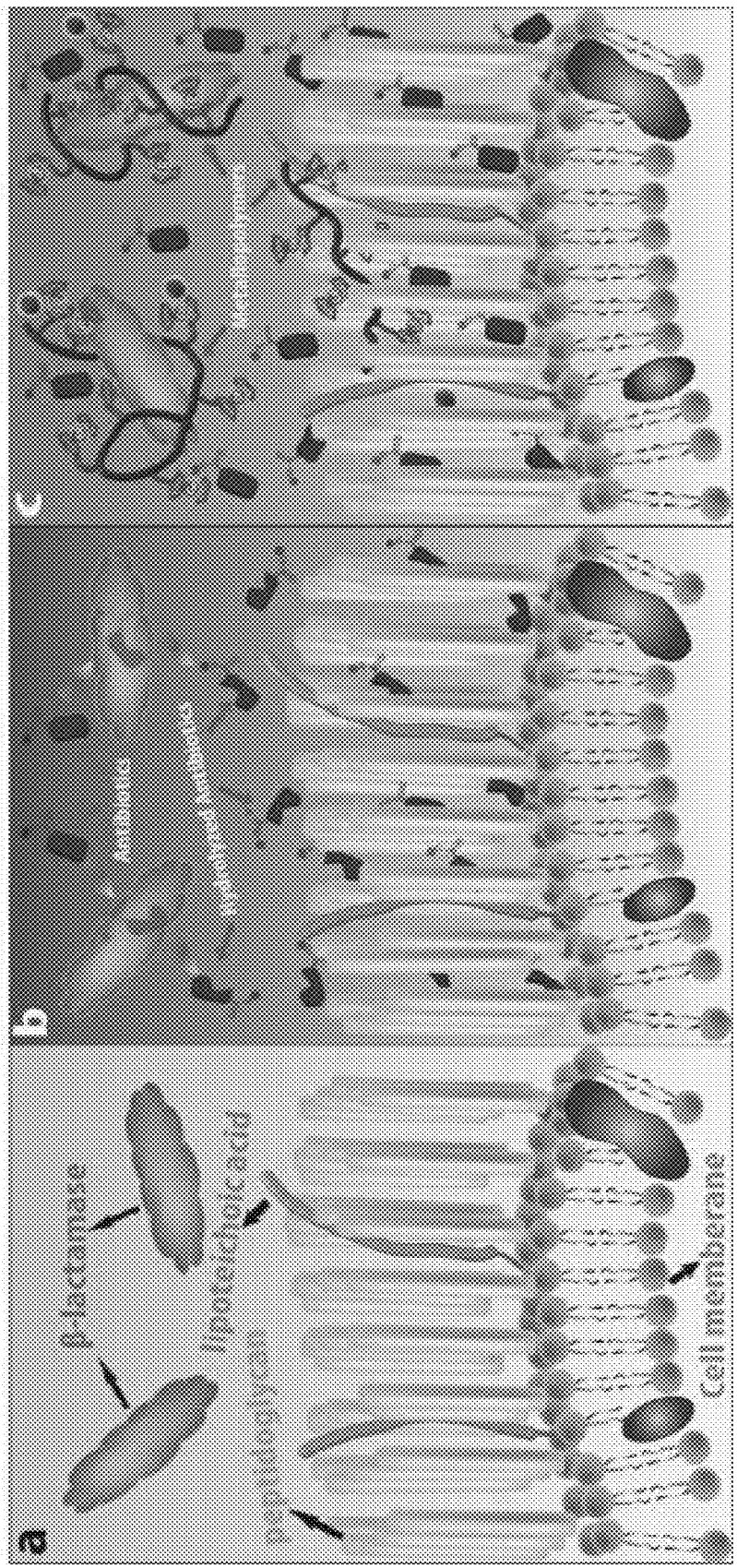
FIG. 11A shows an illustration of several key interactions involving β-lactamase and β-lactam antibiotics with MRSA cells.
FIG. 11B shows an illustration of several key interactions involving β-lactamase and β-lactam antibiotics with typical β-lactamase hydrolysis of β-lactam antibiotics.
FIG. 11C shows an illustration of proposed interactions interactions between β-lactam antibiotics-metallopolymers bioconjugates, β-lactamase and cell wall.
Figure 13C:
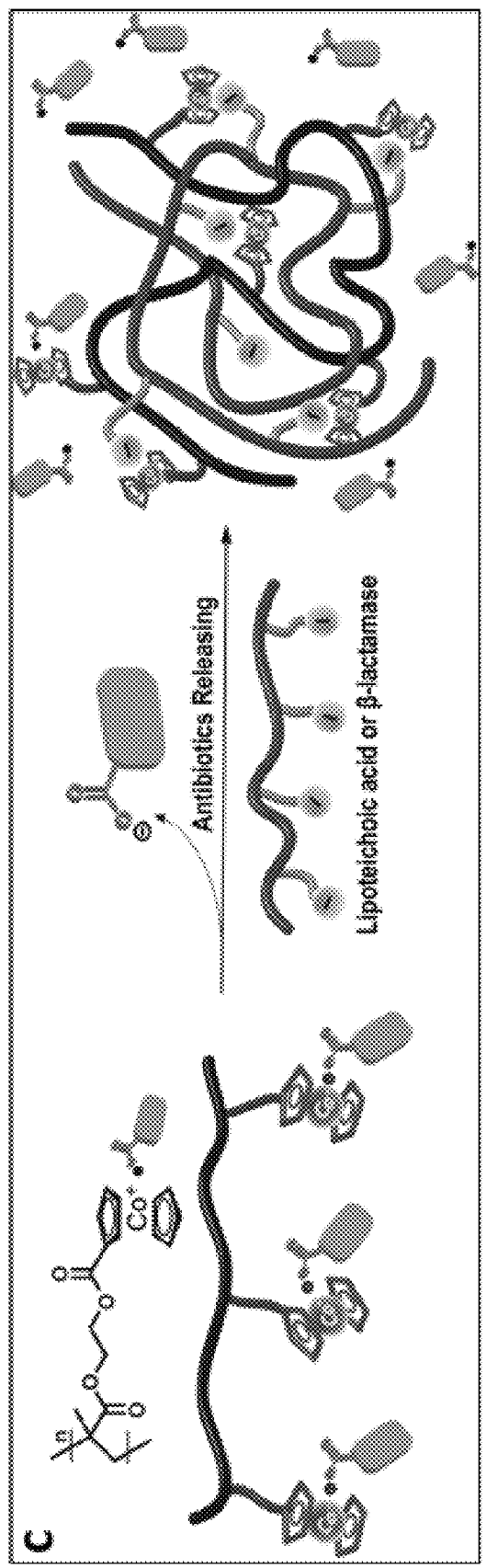
FIG. 13C shows a schematic of antibiotic release from antibiotic-metallopolymers ion-pairs via lipoteichoic acid or β-lactamases.
Figure 13D:
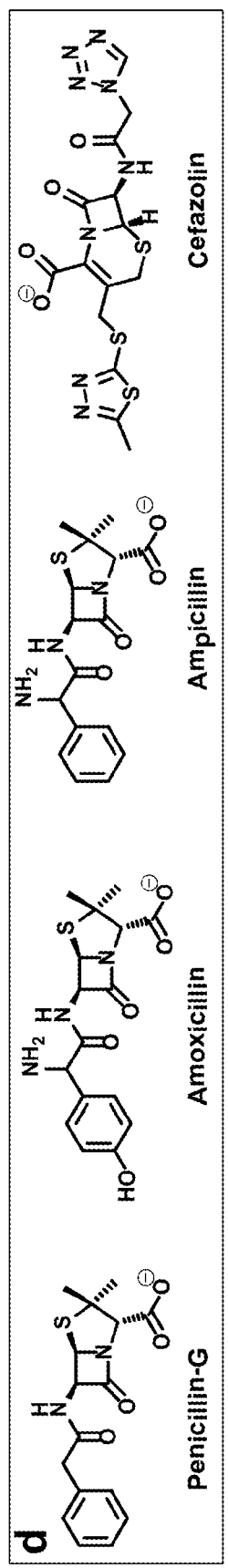
FIG. 13D shows four β-lactam antibiotics used according to the Examples.

Considering the similarity in structure between nitrocefin and other β-lactam antibiotics, cationic cobaltocenium-containing polymers could be extended to protect other conventional β-lactam antibiotics using a similar approach (FIGS. 13A and 13D). As indicated by $^1$H NMR analysis, penicillin-G, cefazolin, amoxicillin and ampicillin can form conjugates with cationic metallopolymers. Furthermore, it was found that antibiotics were released, when antibiotic-metallopolymer bioconjugates performed ion-exchange with negatively-charged cell walls or with carboxylate anions in extracellular solution (FIG. 13C). We carried out model studies to mimic interactions between cationic cobaltocenium-containing polymers and cell walls, as well as β-lactamase. Lipoteichoic acid was chosen as it critically contributes to the negative charge of cell wall (FIGS. 11A-11C). We also selected poly(acrylic acid), as its $pK_a$ (≈4.2) is very similar to that of $Glu_{166}$ in β-lactamase scaffold. Interestingly, the results showed that the ion-pair interactions can enable lipoteichoic acid or β-lactamase to bind with these metallopolymers and subsequently release previously-complexed β-lactam antibiotics (FIG. 13C).

Figure 14A:
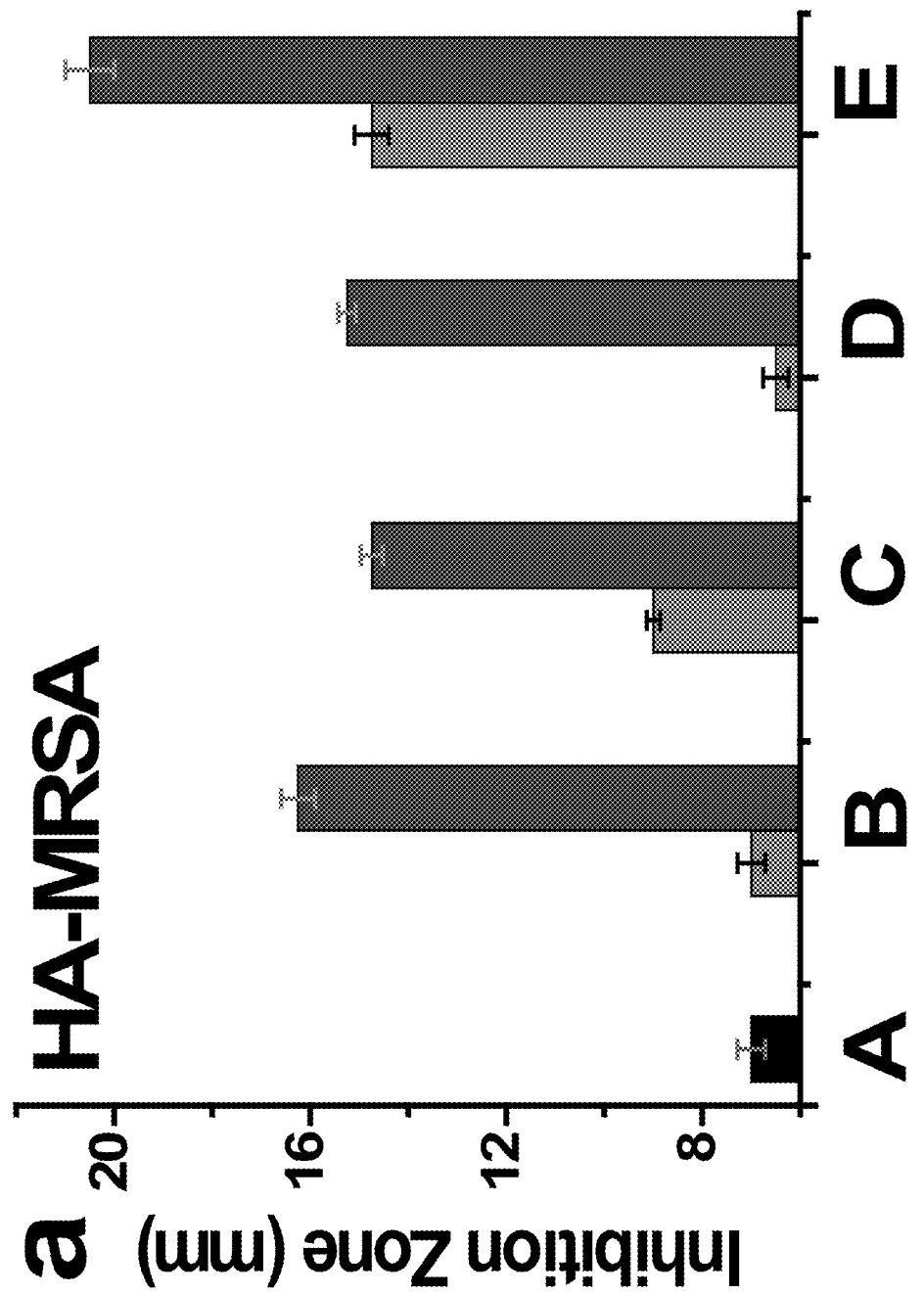
FIGS. 14A, 14B, and 14C shows results of disk-diffusion assays to test antimicrobial effects of conventional antibiotics (left bar in each column B-E), $Cl^-$ paired metallopolymers (control bar labeled under column A in each graph), and their conjugates (right bar in each column B-E) against HA-MRSA, CA-MRSA, and MRSA-252, respectively (concentrations of metallopolymer were 1~2.2 μM).
Figure 14B:
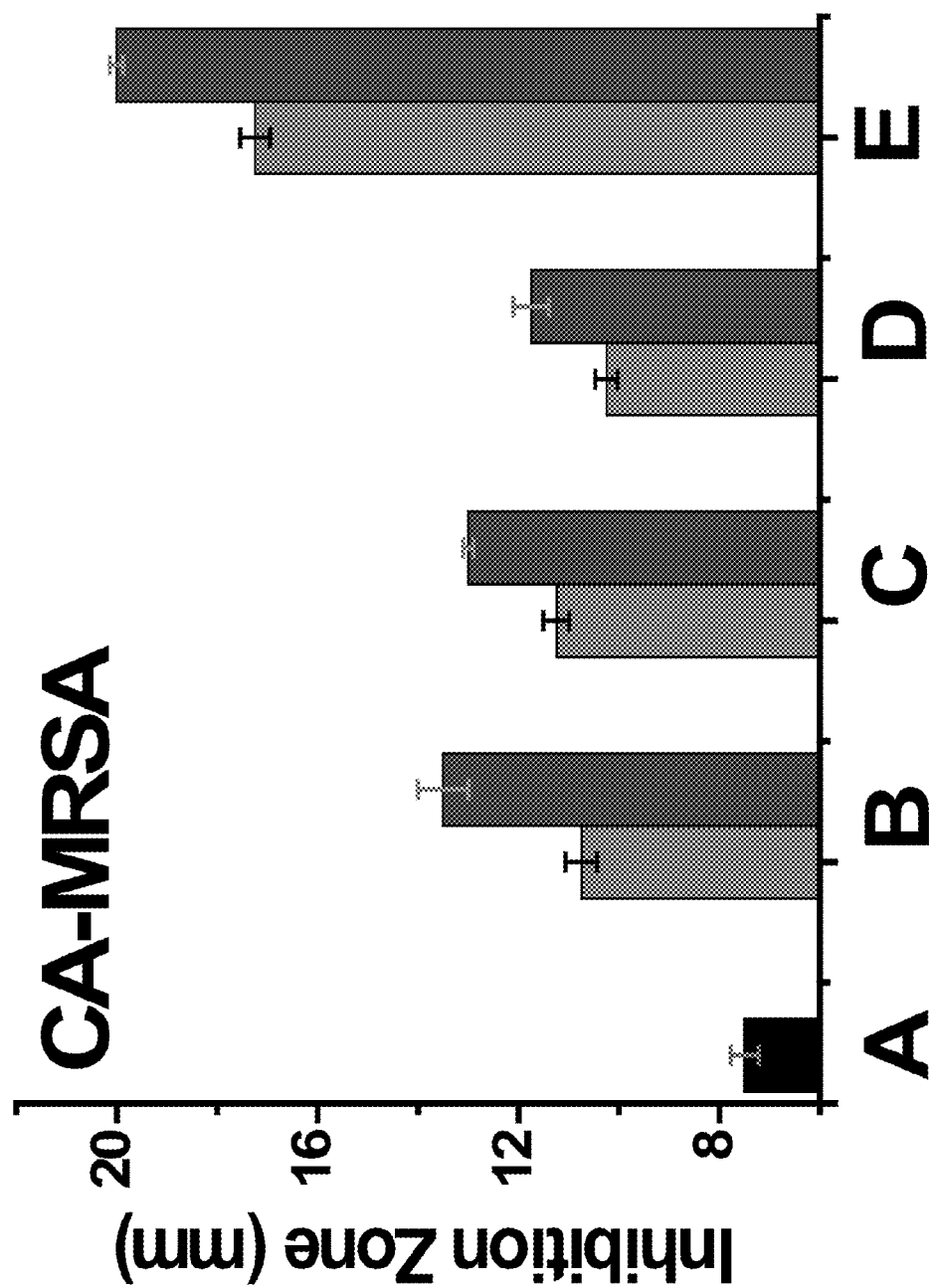
Figure 14C:
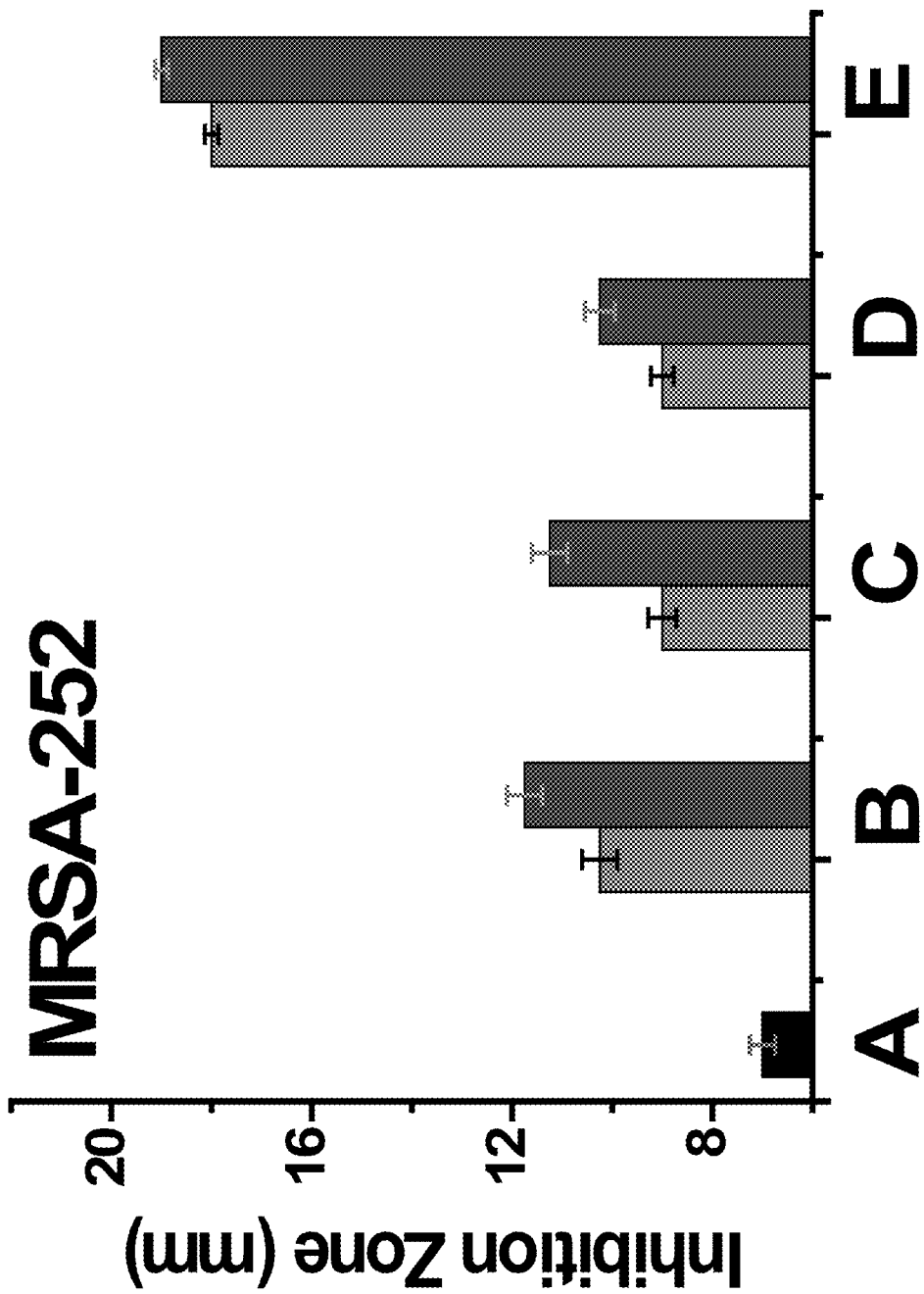

Disk-diffusion assays were used to evaluate the antimicrobial activities of penicillin-G, cefazolin, amoxicillin, ampicillin and their bioconjugates with cobaltocenium-containing polymers against drug-resistant MRSA cells (FIG. 14A-14C). Three different strains of MRSA, including community-associated MRSA (CA-MRSA) (ATCC 1717), HA-MRSA (ATCC 29213) and MRSA-252 (ATCC 1720), were incubated for 24 hours with antibiotics only, Cl$^-$-paired metallopolymers only, and a mixture of the two components. For mixtures of two components, the molar ratio of cobaltocenium moieties to antibiotics was controlled at >1:1, recognizing that in extracellular solution, species with carboxylate groups would complex with cobaltocenium moieties. Cl$^-$-metallopolymers and antibiotics were mixed to form stable antibiotic-metallopolymer ion-pairs before being added to the disks. As shown in FIGS. 14A-14C, at a concentration of 1~2.2 μM, metallopolymers alone showed very little inhibition against MRSA cells, while most antibiotics alone also exhibited low toxicity. However, their corresponding bioconjugates showed significantly enhanced effects in activities against different strains of MRSA, especially for HA-MRSA. The growth of CA-MRSA and MRSA-252 was also inhibited, but to a lesser extent than HA-MRSA, which may be due to other resistant mechanisms in CA-MRSA and MRSA-252. The inhibition of HA-MRSA growth was also observed by confocal scanning laser microscopy (CSLM) and scanning electron microscopy (SEM) imaging.

Figure 15B:
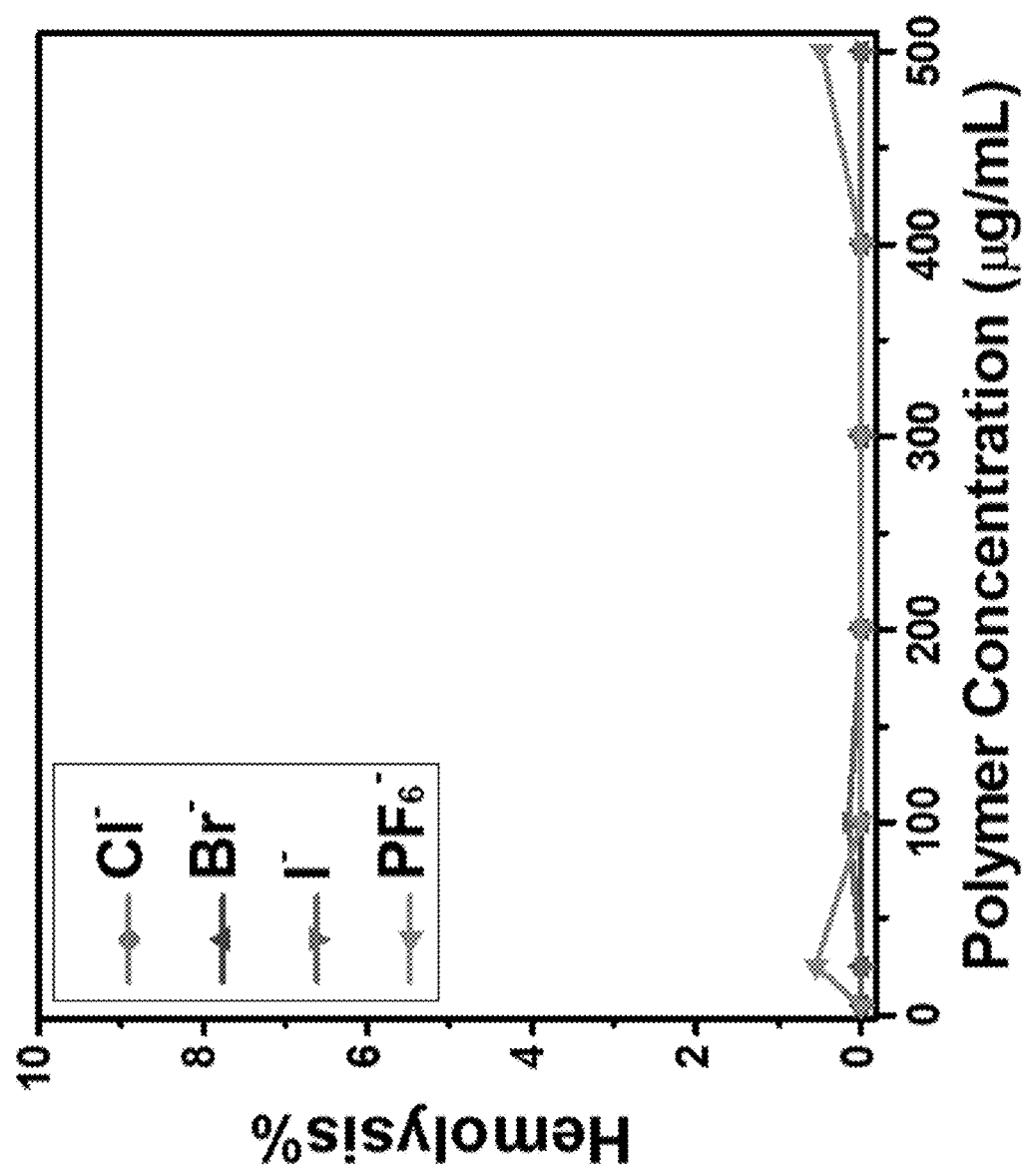
FIG. 15B shows hemolytic activities of halide-paired cationic cobaltocenium-containing polymers against mouse red blood cells.
Figure 15C:
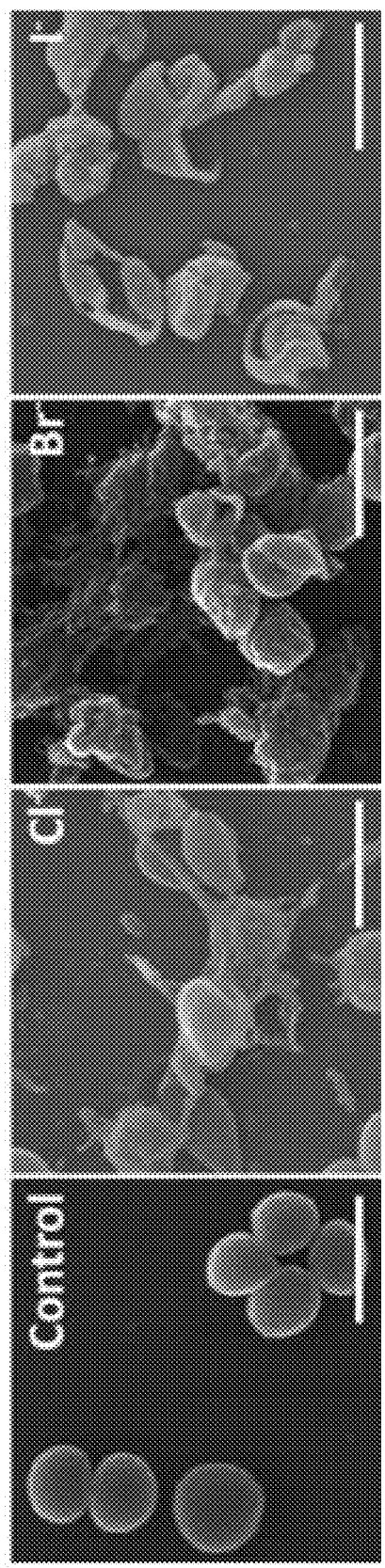
FIG. 15C shows SEM images of HA-MRSA cells before (control) and after incubation with halide-paired cobaltocenium-containing polymers at 5 μM for 9 hours (scale bars represent 1 μm).

It was further discovered that these cationic metallopolymers themselves also showed efficient inhibition against different MRSA cells when their concentrations were increased to about 5 μM (3~5 times of their concentrations in the above antibiotic-metallopolymer bioconjugate study). This is different from other types of β-lactamase inhibitors, as they are mostly non-antimicrobial. The inhibitory concentration ($IC_{90}$) of each halide-paired cobalt-containing polymer was determined for methicillin-sensitive *Staphylococcus aureus* (MSSA, ATCC–1718), HA-MRSA, CA-MRSA, and MRSA-252. As shown in FIG. 14A, both Br$^-$ and Cl$^-$-paired metallopolymers have $IC_{90}$ values at 3~5 μM against HA-MRSA, CA-MRSA, and MRSA-252, while only 1.00 μM against MSSA cells. I$^-$-paired metallopolymers are slightly less effective, while $PF_6^-$-paired cobaltocenium-containing polymers showed much weaker antimicrobial effects, mostly due to their limited solubility in aqueous media. Compared with other cationic antimicrobial polymers, these metallopolymers showed comparable or even lower minimum inhibitory concentrations (15-100 μg/mL) against bacteria. SEM was utilized to illustrate the influence of halide-paired cationic cobaltocenium-containing polymers on MRSA cell membranes. FIG. 15C shows representative images of HA-MRSA cells treated with halide-paired cationic metallopolymers. Compared to control cells, all MRSA cells exhibited partial or complete membrane lysis. Through electrostatic interactions, cationic cobaltocenium-containing polymers could adsorb to the negatively-charged MRSA cell walls, damage the cell wells, and thus lead to cell death, similar to other cationic antimicrobial polymers.

Although these cationic metallopolymers exhibited excellent abilities to lyse microbial cells, they showed negligible hemolytic effects on red blood cells. As shown in FIG. 15B, halide-paired metallopolymers showed extremely low levels of hemolysis (less than 1%) at concentrations up to 500 μg/mL for metallopolymers (~40 μM for Cl$^-$-paired cobaltocenium-containing polymers). This result is important because it indicates our metallopolymers exhibit an extremely low cytotoxicity to red blood cells, and a high selectivity against bacterial cells. Furthermore, cytotoxicity of these metallopolymers was also investigated in in vitro and in vivo tests, which indicated little toxicity.

In conclusion, a class of metallopolymers, cobaltocenium-containing polymers, was discovered to form bioconjugates with various β-lactam antibiotics, including penicillin, ampicillin, amoxicillin and cefazolin, via ionic complexation. These antibiotic-metallopolymer bioconjugates showed high resistance towards β-lactamase-assisted hydrolysis of β-lactam antibiotics and significantly improved efficacy against various strains of MRSA cells over conventional antibiotics. In addition, these metallopolymers themselves, at higher concentrations, also showed excellent antimicrobial activities against different strains of MRSA by selectively disrupting their cell membranes, while maintaining extremely low cytotoxicity against red blood cells and low in vivo toxicity. These discoveries could pave a new platform to design antibiotics and antimicrobial agents to battle multidrug resistant bacteria and superbugs.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A anion-paired metallocene-containing polymer, comprising; at least one monomeric unit comprising a cationic metallocene moiety paired to an anion, wherein the cationic metallocene moiety comprises two cyclopentadienyl anions bound to a metal center in the oxidation state I, and wherein the anion comprises an anionic antibiotic compound.

2. The anion-paired metallocene-containing polymer of claim 1, wherein the anion comprises a hexafluorophosphate anion, a tetraphenylborate anion, a tetrafluoroborate anion, a trifluoromethanesulfonate anion, F—, Cl—, Br—, I—, NO3-, an acetate anion, a sulfate anion, a hydrogen sulfate anion, a perchlorate anion, a bromate anion, a cyanide anion, a thiocyanate anion, a hydroxide anion, a dihydrogen phosphate anion, or a formate anion.

3. The anion-paired metallocene-containing polymer of claim 1, wherein the anionic antibiotic compound comprises a penicillin anion or related compound, a carbapenem anion or related compound, or a cephalosporin anion or related compound.

4. The anion-paired metallocene-containing polymer of claim 1, wherein the metal center comprises comprises iron, cobalt, rhodium, or ruthenium.

5. The anion-paired metallocene-containing polymer of claim 1, wherein the anion-paired metallocene-containing polymer is a homopolymer.

6. The anion-paired metallocene-containing polymer of claim 1, wherein the anion-paired metallocene-containing polymer is a copolymer comprising the at least one monomeric unit comprising the cationic metallocene moiety paired to the anion and a comonomeric unit.

* * * * *